United States Patent
Khachaturov

(10) Patent No.: US 9,538,910 B2
(45) Date of Patent: Jan. 10, 2017

(54) ADJUSTABLE PROBE

(71) Applicant: LUMENIS LTD., Yokneam Ilit (IL)

(72) Inventor: Arkady Khachaturov, Haifa (IL)

(73) Assignee: LUMENIS LTD., Yokneam Ilit (IL)

( * ) Notice: Subject to any disclaimer, the term of this patent is extended or adjusted under 35 U.S.C. 154(b) by 316 days.

(21) Appl. No.: 14/250,582

(22) Filed: Apr. 11, 2014

(65) Prior Publication Data

US 2014/0309493 A1 Oct. 16, 2014

(30) Foreign Application Priority Data

Apr. 11, 2013 (GB) .................................. 1306587.5

(51) Int. Cl.
| | | |
|---|---|---|
| A61B 1/07 | (2006.01) | |
| A61B 18/22 | (2006.01) | |
| A61B 18/20 | (2006.01) | |
| A61B 18/00 | (2006.01) | |

(52) U.S. Cl.
CPC .................. *A61B 1/07* (2013.01); *A61B 18/22* (2013.01); *A61B 2018/00547* (2013.01); *A61B 2018/2035* (2013.01)

(58) Field of Classification Search
USPC ........ 600/106–108, 114, 121–125, 139–142; 606/1–26
See application file for complete search history.

(56) References Cited

U.S. PATENT DOCUMENTS

| | | | | |
|---|---|---|---|---|
| 5,607,435 A * | 3/1997 | Sachdeva | ............. | A61B 1/0058 359/819 |
| 6,106,521 A * | 8/2000 | Blewett | ............. | A61B 18/1477 600/105 |
| 6,277,064 B1 * | 8/2001 | Yoon | ................... | A61B 1/00177 600/104 |
| 8,684,912 B2 * | 4/2014 | Deviere | ............. | A61B 1/00087 600/104 |
| 8,727,966 B2 * | 5/2014 | Rogers | ............... | A61B 1/00098 600/106 |
| 2004/0138529 A1 * | 7/2004 | Wiltshire | ............. | A61B 1/0055 600/144 |
| 2005/0096502 A1 * | 5/2005 | Khalili | ................... | A61B 1/018 600/106 |
| 2008/0065105 A1 * | 3/2008 | Larkin | ............... | A61B 1/00087 606/130 |
| 2009/0299352 A1 | 12/2009 | Zerfas et al. | | |
| 2011/0098529 A1 * | 4/2011 | Ostrovsky | ............ | A61B 1/0008 600/104 |

FOREIGN PATENT DOCUMENTS

EP 1719482 11/2006

OTHER PUBLICATIONS

GB Search Report—Corresponding Application No. 1306587.5 dated Sep. 26, 2013.

* cited by examiner

*Primary Examiner* — Matthew J Kasztejna
(74) *Attorney, Agent, or Firm* — ISUS Intellectual Property

(57) ABSTRACT

An optical fiber endoscopic probe used to deliver radiation, in particular laser radiation, during a surgical procedure. The configuration of components of the endoscopic probe in use is adjustable so as to direct the radiation which exits the fiber as desired. The present invention also relates to a device used to direct the exiting beam of radiation in such an endoscopic probe, which may in particular be used in a narrow probe channel, for example for prostate laser surgery, and to a method of surgical treatment using the endoscopic probe.

23 Claims, 7 Drawing Sheets

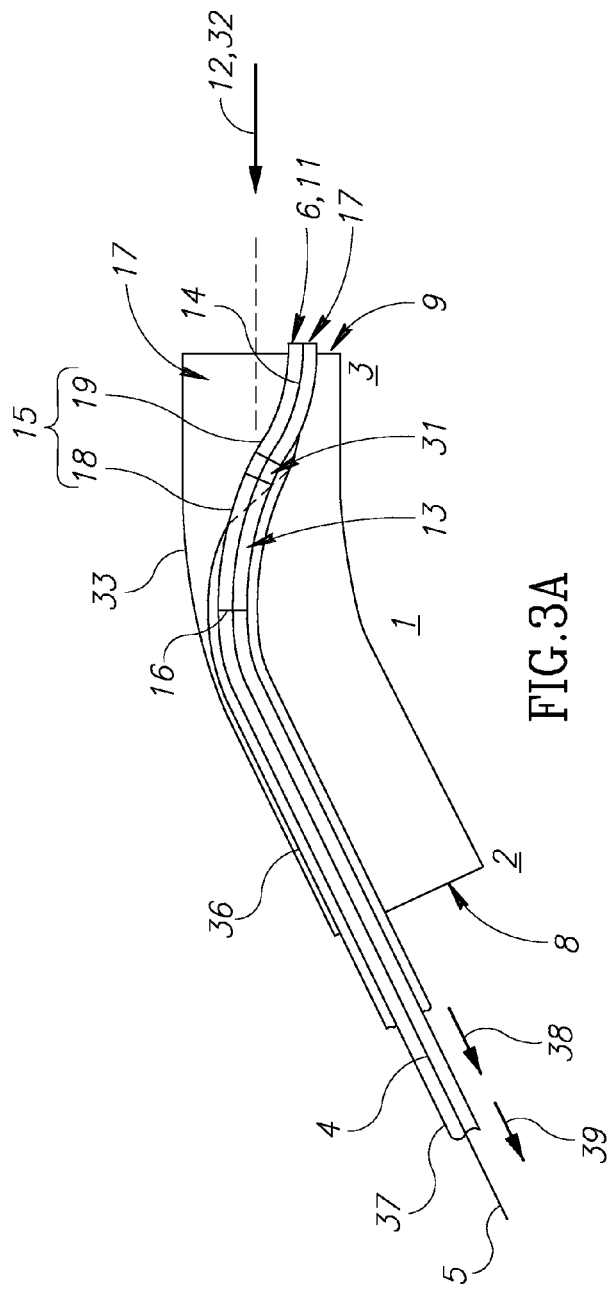
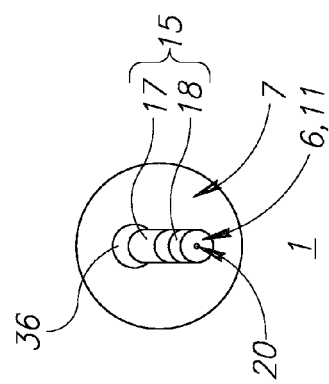
FIG.3A
FIG.3B

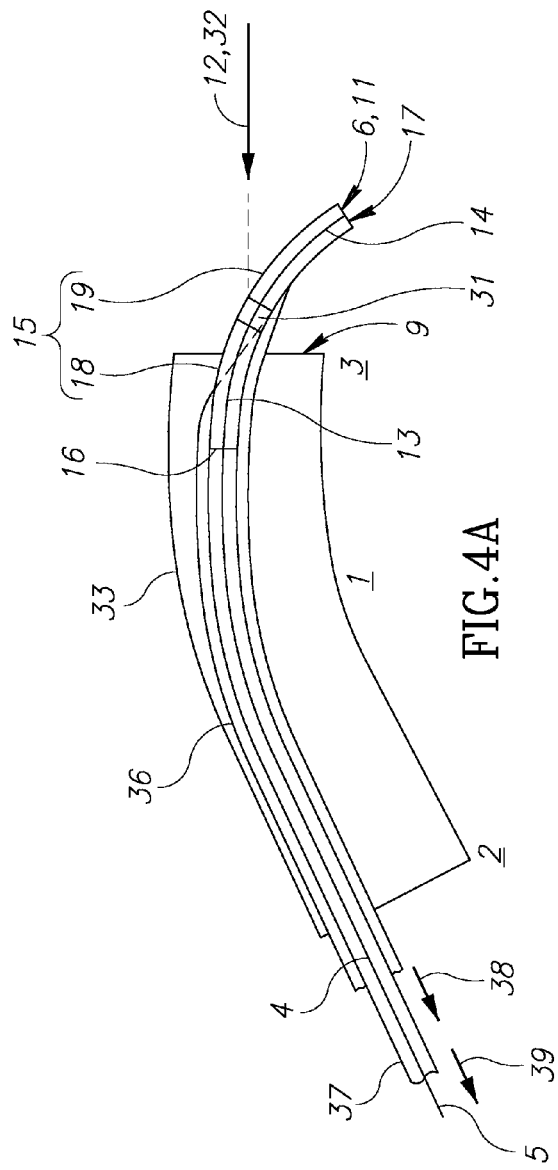
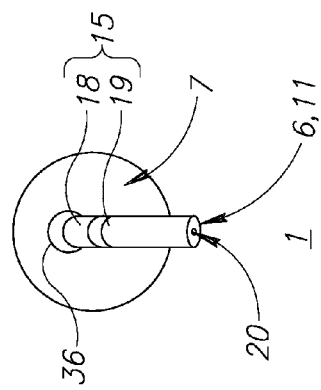
FIG.4A
FIG.4B

ADJUSTABLE PROBE

FIELD OF THE INVENTION

The present invention relates to an endoscopic probe used to deliver radiation, in particular laser radiation during a surgical procedure. The configuration of components of the endoscopic probe in use is adjustable so as to direct the radiation which exits the fibre as desired. The present invention also relates to a device used to direct the exiting beam of radiation in such an endoscopic probe, and to a method of surgical treatment using the endoscopic probe.

The term 'curved', when used herein with reference to curved portions of a waveguide (as defined below), and the curved sections of the adjustable means, means that the respective integer has a major curvature, which is other than the minor curvature of the (often) tubular surfaces of the integer.

The term 'longitudinal axis', when used herein with reference to any point along an endoscopic probe of the present invention, the elongate channel of the probe, the optical fibre or the adjustable means used with the probe, means the longitudinal axis of the respective integer at that point if the integer is straight at that point, and a tangential axis at that point, if the integer is curved at that point. The term is more often used in respect of the distal end of the integer in use.

The terms 'mutually rotatable' and 'mutual rotation', when used herein with reference to adjacent curved sections of a sheath, mean rotatable and rotation respectively about a common axis at a point of adjacency (as defined).

The term 'point of adjacency', when used herein with reference to adjacent curved sections of a sheath, means a point at which the sections are adjacent through abutting and/or overlapping each other, and/or by an end of one section housing an end of the other, or are otherwise adjacent.

The term 'sheath', when used herein with reference to a sheath or the first and/or second adjacent curved sections of a sheath in an adjustable means includes
a) a reference to a full sheath, meaning
  i) one in which a conduit in the sheath or a first and/or second curved section of the sheath fully encloses a waveguide in the form of an optical fibre for delivering light to the delivery end thereof, or
  j) one in which the sheath or a first and/or second curved section of the sheath comprises a waveguide in the form of a hollow light guide for delivering light to the delivery end thereof; and
b) a reference to a partial sheath, meaning one in which an open groove in the sheath or a first and/or second curved section of the sheath supports an optical fibre or hollow light guide for delivering light to the delivery end thereof; and has securing means, such as arches, spanning the optical fibre to conform the fibre to the section of the sheath which supports the fibre or hollow light guide.

The term 'sigmoid', when used herein with reference to an adjustable means in a first configuration means S-shaped.

The term 'waveguide', when used herein with reference to an adjustable means, means any elongate integer which permits the transmission of light and which has surfaces which in use internally reflect light travelling down the integer from a proximal input end to exit the integer from a distal delivery end. The term thus includes a relatively flexible optical fibre and a relatively rigid, self-supporting integer with a conduit therethrough with surfaces which in use internally reflect light travelling down the conduit in the integer (a 'hollow light guide').

BACKGROUND OF THE INVENTION

In surgery, in particular endoscopic surgery, flexible optical fibres are often used to deliver laser light from a laser device to a treatment site to ablate, cauterise, dissect, excise and/or resect hard or soft tissue. In use, the fibre is typically passed down an elongate channel in the probe until its distal delivery end projects out of the distal end of the elongate channel of the probe.

In some probes, typically in orthopaedic procedures, the laser beam preferably travels from the delivery end of the fibre substantially parallel to the longitudinal axis of a probe or channel, each of which is straight throughout its length. In other procedures, it is desirable to direct the exiting beam skewed to the axis of such a probe or channel, so that, for example soft, tissue which is alongside the probe can be treated.

Hitherto, the design of the latter type of probes has been dictated by the direction in which the exiting beam is required to travel respect to the elongate channel of the probe, and the desired direction of the exiting beam is not readily adjustable in such probes. Thus, a wide variety of probes has had to have been developed, each specific to a particular endoscopic surgical procedure and the desired direction of the exiting beam. This is a first technical problem over a large range of probes known in the art.

A similar second technical problem to that described above arises in multichannel endoscopic probes which comprise an elongate working channel for a variety of non-laser surgical equipment for ablating, dissecting, excising and/or resecting hard or soft tissue, where it is desired to illuminate the treatment site from various directions. This may be effected by for example using a flexible optical fibre in an auxiliary channel in the probe to deliver visible non-coherent light in a beam in the various directions, in particular in desired directions not specific to any one procedure.

Thus, it would be desirable to provide an endoscopic probe in which the delivery end of the fibre may be readily set at positions and configurations such that light which exits the fibre through its delivery end is in a desired direction. It would further be desirable to provide a versatile endoscopic probe which could provide an orientation of the delivery end required by a wide variety of procedures, so that a single probe may be used in such procedures.

Many endoscopic procedures, for example laser ablation of the prostate (LAP), such as holmium Laser Ablation of the Prostate (HoLAP) require any probe and elongate channel in the probe to be narrow.

The minimum dimension in the transverse direction of the elongate channel of the probe may typically be less than that of the space occupied by the distal delivery end of the fibre when deployed beyond the distal end of the channel and/or the probe, generally skewed to the longitudinal axis of the channel and/or the probe at their distal ends. This is a second technical problem which arises in providing a solution to the first technical problem.

Again, a similar second technical problem to that described above arises in multichannel endoscopic probes which comprise an elongate working channel for a variety of non-laser surgical equipment, where any such probe and any elongate channel in the probe are required to be narrow, but where it is desired to illuminate the treatment site from various directions. This may be effected by for example using a flexible optical fibre in a narrow auxiliary channel in the probe to deliver a visible non-coherent light beam in the various directions.

It will be seen that the second technical problem arises in providing a solution to the first technical problem for narrow probes We have now found a solution which solves both the first and second technical problems.

SUMMARY OF THE INVENTION

A first aspect of the present invention provides an endoscopic probe for delivering light, which comprises an elongate channel which in use surrounds at least a large proportion of an optical fibre having a proximal input end and a distal delivery end, with the delivery end characterised by an adjustable means which can be adjusted to direct light travelling down the fibre in any desired direction.

In a second aspect, the present invention provides an optical fibre device for delivering light, which comprises an optical fibre with an input end and a delivery end, with the delivery end characterised by an adjustable means which is adjustable to direct light travelling down the fibre in a desired direction.

In a third aspect, the present invention provides a method of treatment which comprises the use of an endoscopic probe of the first aspect of the present invention.

DETAILED DESCRIPTION OF THE INVENTION

Accordingly, a first aspect of the present invention provides an endoscopic probe for delivering light, which comprises an elongate channel which in use surrounds at least a large proportion of an optical fibre having a proximal input end and a distal delivery end, with the delivery end characterised by an adjustable means which can be adjusted to direct light travelling down the fibre in any desired direction.

The endoscopic probe of the present invention may be used to deliver laser light from a laser device to operate surgically on hard or soft tissue at a treatment site, by using a flexible optical fibre in a working channel in the probe. It will be appreciated that it may also be used to deliver a visible non-coherent light beam to illuminate a treatment site from various directions, by using a flexible optical fibre in an auxiliary channel.

In all forms of the present invention, the probe may be tapered, bevelled and/or chamfered at its distal end, which may lead to desirably enhanced ease of insertion of the probe and minimisation of the amount of damage to surrounding tissue and/or treatment sites and/or to the endoscope wall during insertion. It may be straight throughout the most part of its length and/or curved, typically towards its distal end; the curvature of any such curved portions will preferably be gradual and may be slight.

The probe may be a conventional endoscopic probe, typically tubular, preferably cylindrical with a constant round cross-section, for example an elliptical or oval cross-section, but in particular a circular, cross-section.

In use of the endoscopic probe of the first aspect of the present invention
i) the adjustable means in its first configuration at the distal delivery end of the optical fibre is slid into the channel of the probe from its proximal end to at least partially beyond its distal end, iii) the adjustable means is adjusted to the second configuration, so as to direct light travelling down the fibre which exits the adjustable means through its distal delivery end in any desired direction.

The above steps are reversed to remove the adjustable means at the distal delivery end of the fibre from the channel of the probe through its proximal end.

The adjustment of the adjustable means between the first configuration and the second configuration is applicable to any probe with a channel for an optical fibre.

The channel of the probe may have a non-uniform bore from its proximal end to its distal end, but the channel of the probe may typically have a uniform bore from its proximal end to its distal end.

It will typically conform to the probe, and thus for example may be straight throughout the most part of its length and/or curved, typically towards its distal end; the curvature of any such curved portions will preferably be gradual and may be slight. Its longitudinal axis at points along its length (straight and/or curved) may coincide with, or run in a direction parallel to a longitudinal axis of the probe at points along its length (straight and/or curved). It has an open proximal, first end and an open distal, second end.

The channel may be a conventional endoscopic probe channel, typically tubular, preferably cylindrical with a constant round cross-section, for example an elliptical or oval cross-section, but in particular a circular, cross-section.

As noted above, within the general scope of the present invention, the elongate channel which in use surrounds at least a large proportion of the optical fibre need not be narrow, and for example its minimum dimension in a transverse direction to its longitudinal axis at any point may be from 10 to 15 mm, for example from 12 to 13 mm. There is also no requirement that the first configuration and second configuration differ from each other in their respective dimension in a transverse direction to the longitudinal axis of the elongate channel of the probe at any point. There is also, for example, no requirement that the former should be less than the latter.

The main requirements within the general scope of the present invention are that
a) adjustment of the adjustable means between the first configuration and the second configuration enables light travelling down the fibre which exits the adjustable means to be directed in any desired direction, typically skewed to the longitudinal axis of the channel and/or the probe at their distal ends, and
b) the dimension of the first configuration in a transverse direction to the longitudinal axis of the elongate channel of the probe at any point must be less than the minimum cross-dimension of the channel at that point, to allow the adjustable means of the present invention to pass from the open proximal, first end to the open distal, second end of the channel and the treatment site, Where the channel is curved at any point, and the dimension of the first configuration in a transverse direction to the longitudinal axis of the elongate channel of the adjustable means at any point is comparable with the minimum cross-dimension of the channel at that point, curvature of any such point will preferably be gradual. It will be apparent that, if there are tight curves in the elongate channel, the adjustable means in its first configuration may jam between the outer and inner curved faces of the bore of the channel at the curve.

Alternatively or additionally, the length and the dimension of the adjustable means in a transverse direction to a longitudinal axis at any point of the channel may have to be limited to give sufficient transverse play of the adjustable means in the curved section of the elongate channel for the means to be able to negotiate the curved section.

The design of the probe should be such that the adjustable means does not jam in, and is able to negotiate, any curved section of the channel.

The manner in which the design is dictated by the interaction of the dimensions of the bore of the channel and of the curvature of any curved parts of the channel, and the length and the dimension of the adjustable means in a transverse direction to a longitudinal axis at any point of the channel in its first configuration will be known to, or will be readily deducible by, one skilled in the art of endoscopic probe design.

Within the general scope of the present invention, the dimension of the second configuration in a transverse direction to the longitudinal axis of the elongate channel of the probe at its distal end may be greater or less than or the same as the above minimum cross-dimension of the channel.

It will be appreciated that within the general scope of the present invention, the endoscopic probe of the present invention provides a solution to the first technical problem for endoscopic probes in general.

The desired direction of the beam of light exiting the adjustable means may be readily varied and controlled, in particular in endoscopic surgical procedures, in a versatile manner to target specific tissue and/or treatment sites. It thus provides a versatile endoscopic probe which may be used in a wide variety of, in particular endoscopic, laser surgical procedures without being specific to any one procedure.

It is also more economical to fabricate a single probe which may be used in a wide variety of surgical procedures rather than by fabricating a wide variety of probes for a wide variety of specific surgical procedures.

As noted above, many endoscopic procedures, for example laser ablation of the prostate (LAP), such as holmium Laser Ablation of the Prostate (HoLAP) require any probe and elongate channel in the probe to be narrow. The first aspect of the present invention is particularly applicable when the probe delivers laser light from a laser device through a probe which comprises a narrow elongate channel which in use surrounds at least a large proportion of the optical fibre.

It will be appreciated that the endoscopic probe of the present invention provides a solution to the second technical problem for endoscopic probes which have a narrow channel.

Accordingly, in a preferred form, the endoscopic probe comprises a narrow elongate channel which in use surrounds at least a large proportion of the optical fibre, and the adjustable means can be adjusted
a) from a first configuration with a dimension in a transverse direction to the longitudinal axis of the elongate channel of the probe at its narrowest point which is less than the minimum cross-dimension of the channel at that point
b) to a second configuration with a dimension in a transverse direction to the longitudinal axis of the elongate channel of the probe at its distal end which is greater than the above minimum cross-dimension of the channel.

In use of this preferred form, where the elongate channel which in use surrounds at least a large proportion of the optical fibre is narrow:
i) the adjustable means is adjusted to the first configuration (smaller that the channel of the probe at its narrowest point);
ii) the adjustable means at the distal delivery end of the optical fibre is slid into the channel of the probe from its proximal end to at least partially beyond its distal end,
iii) the adjustable means is adjusted
   a) to the second configuration (larger that the channel of the probe at its narrowest point),
   b) so as to direct light travelling down the fibre which exits the adjustable means in any desired direction.

The above steps are reversed to remove the adjustable means at the distal end of the fibre from the channel of the probe through its proximal end.

The adjustment of the dimension in a transverse direction to a longitudinal axis of the channel between first and second configurations of the adjustable means is applicable to any probe with a narrow channel for the optical fibre.

The second technical problem addressed by the present invention is
a) to be able to pass such an optical fibre from the open proximal, first end to the open distal, second end of the channel, following insertion of the probe into the incision, and
b) to allow access of light through the fibre to the treatment site in a desired direction, which is achieved by means of the adjustable means of the present invention.

It will be appreciated that the endoscopic probe of this preferred form of the present invention provides a solution to the second technical problem.

It is also advantageous that the solutions to both technical problems may be provided as described hereinbefore using conventional endoscopic probes.

Typical dimensions for such a narrow channel for the optical fibre in a narrow probe may be 10 to 40 for example 15 to 25 mm in overall length (straight and/or curved) and 3 to 7 mm, for example about 5 mm overall in a transverse direction to its longitudinal axis (as defined) at any point.

The narrow channel of the probe may have a non-uniform bore from its proximal end to its distal end. The first configuration and second configuration (when the means is deployed in use at least partially beyond the distal end of the narrow channel) of the adjustable means will then have a dimension in a transverse direction to the longitudinal axis of the elongate channel of the probe at any point which is respectively less than or greater than the bore of the channel of the probe at its narrowest point.

The narrow channel of the probe typically has a uniform bore from its proximal end to its distal end. The first configuration and second configuration of the adjustable means will then have a dimension in a transverse direction to the longitudinal axis of the elongate channel of the probe at any point which is respectively less than or greater than the bore of the channel in the probe. It will typically conform to the probe, and thus for example may be straight throughout the most part of its length and/or curved, typically towards its distal end. The curvature of any such curved portions will preferably be gradual and may be slight.

Its longitudinal axis at points along its length (straight and/or curved) may coincide with, or run in a direction parallel to a longitudinal axis of the probe at points along its length (straight and/or curved).

Such a narrow elongate channel has an open proximal, first end and an open distal, second end. It is often tubular, preferably cylindrical with a constant round cross-section, for example an elliptical or oval cross-section, but in particular a circular, cross-section, which is preferably of a similar, and especially the same, cross-section throughout. It has an open proximal, first end and an open distal, second end.

As for the general probe of the present invention, the curvature of any curved parts of the channel will preferably be gradual, since with tight curves in the elongate channel, the adjustable means in its first configuration may jam between the outer and inner curved faces of the bore of the channel. Alternatively or additionally, the dimension of the adjustable means in a transverse direction to a longitudinal axis of the channel at any point may have to be limited to give sufficient transverse play of the adjustable means in the curved section of the elongate channel for the means to be able to negotiate the curved section.

Where the channel of the probe has a bore which is narrow and curved at any point (often near its distal end) it will be appreciated that
a) the length of the adjustable means generally along the channel of the probe,
b) its dimension in its first configuration in a transverse direction to the longitudinal axis of the channel of the probe with respect to the curvature at that point, and
c) the curvature at that point
must be such that the adjustable means will not jam between the outer and inner curved faces of the bore of the channel around that point.

The design of the probe should be such that the adjustable means does not jam in, and is able to negotiate, any curved section of the channel. The design is dictated by the interaction of the dimensions of the bore, and of the curvature of any curved parts, of the channel, and the length and the dimension of the adjustable means in a transverse direction to a longitudinal axis at any point of the channel in its first configuration. The manner in which the will be known to, or will be readily deducible by, one skilled in the art of endoscopic probe design.

In use, the outer faces of the probe body, the inner faces of the channel, and at least a large proportion of the adjustable means when it is slid into a narrow channel for the optical fibre are each in sliding contact respectively with surrounding soft tissue, the adjustable means and the channel.

They are therefore in at least a large proportion of their surfaces each preferably independently formed from a biocompatible low-friction material. A low-friction material is of course not necessary elsewhere in the respective integer, but it is often convenient for the rest of each integer to be of such materials. that Suitable materials for use in the above integers of the probe of the present invention include biocompatible plastics materials and biocompatible metallic materials, such as biocompatible stainless steels, with a high surface finish on any such biocompatible metal, over a large proportion of the relevant surfaces. Such plastics materials may also be resiliently elastic, and so may give, to further safeguard surrounding soft tissue, the adjustable means and the channel, as appropriate.

The desired direction of the light travelling down the fibre on exiting the adjustable means at its distal delivery end is parallel or skewed to the initial path of the light on entering the proximal input end of the adjustable means, and preferably skewed to the longitudinal axis of the probe or the channel at its distal end when in use.

In this preferred form, the probe of the present invention is one with a narrow channel for the optical fibre, as described hereinbefore, in which the dimension of the adjustable means may be adjusted between first and second configurations in use, which differ from each other in their respective dimension in a transverse direction to the longitudinal axis of the elongate channel of the probe at any point.

The change from a first configuration to a second configuration which differ from each other in their respective dimension in a transverse direction to the longitudinal axis of the elongate channel of the probe at any point may be carried out in a number of ways. These include the following by way of example only, without in any way limiting the scope and spirit of the present invention:

For example, the adjustable means may be adjusted between first and second configurations in use, by
a) reversibly bending, twisting or otherwise deforming or distorting the adjustable means and/or
b) mutually and reversibly rotating, swivelling or pivoting two or more parts of the adjustable means In a general embodiment of the preferred form (probe with narrow channel), the adjustable means comprises an elongate self-supporting sheath.

Any sheath is generally a full sheath (as defined) which closely houses a waveguide in the form of an optical fibre, and thus shields the fibre of the probe, other than at its distal delivery end, in use in endoscopic surgical procedures from target tissue, treatment sites and/or bodily fluids on the sheath.

In such a full sheath the optical fibre is often continuous and often forms at least a large proportion of the fibre of the probe at or near its distal delivery end. A conduit in the full sheath extends along and closely houses a length of the fibre, which is often continuous. The sheath includes a distal end part which permits the transmission of light therethrough. The flexible fibre essentially follows the internal configuration of the sheath, which thus holds the fibre in a desired configuration. The fibre within the sheath should be attached to the sheath, normally at or near its distal delivery end.

It will be appreciated that, in any embodiment of this form (probe with narrow channel) in which the adjustable means is adjusted between first and second configurations in use by reversibly bending, twisting or otherwise deforming or distorting the adjustable means, these actions may alter the length of the fibre within the sheath as the flexible fibre essentially follows the changing internal configuration of the sheath. In such embodiments of this form, other than at any point of attachment to the sheath (as described above), the fibre should be slidably housed in the sheath.

In any embodiment of this form in which the adjustable means is adjusted between first and second configurations in use by mutually and reversibly rotating, swivelling or pivoting two or more parts of the adjustable means, the fibre may not need to be slidably housed in the sheath.

Alternatively or additionally, the adjustable means may comprise an elongate self-supporting full sheath in which a conduit, with surfaces which in use internally reflect light travelling down the conduit, forms a hollow light guide (as defined).

It will be appreciated that in this embodiment of this form (probe with narrow channel), it may be difficult to provide an adjustable means that may be adjusted between first and second configurations by reversibly bending, twisting or otherwise deforming or distorting it, without impairing the internally reflective surfaces of the hollow light guide conduit. Thus, in general, this embodiment of the preferred form will more often be present when the adjustable means comprises an elongate self-supporting sheath with at least first and/or second curved sections which are mutually rotatable about a common axis at the point of adjacency (as described hereinafter in greater detail).

Where the sheath is a partial sheath (as defined), an open groove in the sheath supports an optical fibre for delivering light to the delivery end thereof, and has at least two securing means, such as arches, spanning the optical fibre to conform the fibre to the sheath or section of the sheath which supports the fibre.

In general, this embodiment of the preferred form (probe with narrow channel) will more often be present when the adjustable means comprises an elongate self-supporting sheath with at least first and/or second curved sections which are mutually rotatable about a common axis at the point of adjacency. In this embodiment of this form, there should be a point of attachment of the fibre to the sheath (as described above), but the fibre may not otherwise need to be slidably housed in the sheath.

It may be possible to provide an adjustable means that may be adjusted between first and second configurations by reversibly bending, twisting or otherwise deforming or distorting it.

However, it will be appreciated that in this embodiment of this form, the fibre should be slidably housed in the sheath, and there will be a risk of it ceasing to conform to the sheath as the latter is reversibly bent, twisted, or otherwise deformed or distorted.

In another embodiment of the preferred form (probe with narrow channel), the sheath comprises an integer which is resiliently elastic and which, for example, may be reversibly deformed between the two configurations by reversibly bending, twisting or otherwise deforming or distorting the integer, rather than by mutually and reversibly rotating, swivelling or pivoting two or more parts of the sheath For example, the sheath may comprise a shape-memory material, for example
i) such a biocompatible plastics material, or
ii) such a biocompatible alloy material,
which are reversibly deformable (the so-called one-way effect), frequently under reversible heating and cooling:

The sheath may alternatively comprise an integer which is resiliently elastic and which, for example may be reversibly deformed between the two configurations, the change from a first configuration to a second configuration placing the integer under resilient stress, which urges it to return to the first configuration, for example a biocompatible laterally deformed helical spring. Other ways in which the adjustable means may be reversibly bent, twisted, or otherwise deformed or distorted from its first configuration to its second configuration when projecting out of the distal end of the elongate channel of the probe will be known to, or will be readily deducible by, one skilled in the art.

In the foregoing alternative forms of the adjustable means, the first configuration will in general be essentially straight and/or slightly curved and may if necessary have a length and dimension in a transverse direction to a longitudinal axis of the channel at all points in the channel that enable it to follow any internal curves of the elongate channel.

The second configuration of the adjustable means at, and projecting out of, the distal end of the elongate channel of the probe will be curved to the extent that it has a dimension in a transverse direction to a longitudinal axis of the channel at its distal end that is sufficient to direct light travelling down the fibre which exits the adjustable means in any desired direction.

The following describes forms of the probe of the present invention in which the adjustable means may be adjusted between first and second configurations in use, by mutually and reversibly rotating, swivelling or pivoting two or more parts of the adjustable means.

This description is directed to adjustable means for a probe of the preferred form with a relatively narrow channel comprising a sheath which extends along and closely houses a waveguide in the form of an optical fibre or a hollow light guide with internally reflective surfaces or consists essentially of a hollow light guide conduit, where the sheath consists essentially of first and second adjacent curved sections which are mutually and reversibly rotatable. The first and second adjacent curved sections are mutually rotatable about a common axis at a point of adjacency.

However, it will be appreciated that in a general form, such a sheath may comprise more than just first and second adjacent curved sections of the sheath. This description, directed to adjustable means comprising a sheath which consists essentially of first and second adjacent curved sections which are mutually and reversibly rotatable, is applicable to any probe with a sheath which comprises more than two curved sections mutatis mutandis. Such sheaths are also suitable for use in a wide or narrow channel The disclosure of sheaths with two sections is made by way of example only, without in any way limiting the scope and spirit of the present invention:

In a third, preferred embodiment of the preferred form of the invention (probe with narrow channel), the adjustable means comprises an elongate full sheath, which extends along and closely houses at least a proportion of a waveguide in the optical fibre, which fibre is continuous and often forms at least a large proportion of the fibre of the probe at or near its distal delivery end.

A conduit in the full sheath extends along and closely houses a length of the fibre. The sheath includes a distal end part which permits the transmission of light therethrough. The flexible fibre essentially follows the internal configuration of the sheath, which thus holds the fibre in a desired configuration.

The fibre within the sheath is attached to the sheath, normally at or near its distal delivery end, and the rest of the fibre may be fixedly or slidably housed in the sheath.

The sheath comprises first and second adjacent curved sections which are mutually and reversibly rotatable. These may be adjacent through abutting and/or overlapping each other, and/or by an end of one section housing an end of the other. at a 'point of adjacency' (as defined). The first and second adjacent curved sections are mutually rotatable about a common axis at the point of adjacency The flexible fibre essentially follows the internal curves of the rigid sheath, and thus comprises first and second adjacent curved portions corresponding to the first and second curved sections of the sheath. The sheath thus holds the portions curved, and includes a distal end part which permits the transmission of light therethrough.

In this embodiment of the preferred form of the endoscopic probe (probe with narrow channel), the first and second curved sections of the sheath are preferably of the same length and curvature as, and define, the length and curvature of, the corresponding first and second curved portions of the fibre. Adjustment of the positions and configurations of the first and second adjacent curved sections of the sheath relative to each other adjusts the positions and configurations of the first and second adjacent curved portions of the fibre in the same way.

Suitable materials for use in the above sheath in the probe of the present invention include known biocompatible plastics materials.

The internal fibre surfaces in use reflect light travelling down the fibre to exit the fibre through a distal end surface thereof in a direction parallel or skewed to its direction at the proximal input end of the fibre.

Hence, the angle between light that has initially entered the proximal input end of the first curved portion of the fibre in the first curved section of the sheath and light that exits the fibre through the distal delivery end of the second curved portion of the fibre in the second adjacent curved section of the sheath will also be adjusted in the same manner.

The fibre in the conduit in the full sheath which extends along and closely houses the fibre is preferably continuous through its first and second adjacent curved portions and preferably forms at least a large proportion of the fibre of the probe at or near its distal delivery end.

The fibre within the sheath in use and elsewhere within the channel towards and/or through its open proximal, first end will normally be a conventional fibre used in conventional endoscopic probes.

The fibre may thus be made of a known biocompatible glass material, such as a sodium silica glass or a borosilicate glass, (or for some applications a fluorozirconate, fluoroaluminate, or chalcogenide glass). The fibre may also be made of a biocompatible plastics material, such as a known step-index multi-mode material.

The fibre may have a constant round cross-section, for example an elliptical or oval cross-section, but in particular a circular cross-section. The diameter of the optical fibre may depend on the particular use contemplated for the probe, for example in laser surgical procedures, or with a visible non-coherent light beam to illuminate a treatment site from various directions, but may suitably be that of optical fibres used in known probes, in particular narrow probes with narrow channels.

The conduit within the first and second adjacent curved sections of the sheath which closely houses the length of fibre will typically conform to the fibre and have a corresponding cross-section or diameter throughout. The diameter of any circular conduit in the sheath may thus suitably slightly exceed that of any known optical fibre used.

Each curved section of the sheath and portion of the fibre preferably has its curvature in a single plane.

In a more preferred embodiment of this form of the endoscopic probe (probe with narrow channel), the first and second curved sections of the sheath and portions of the fibre are of similar, and in particular the same, length and curvature.

In the first configuration (adjustable means smaller than the channel of the probe at its narrowest point), the first and second adjacent curved sections of the sheath and portions of the fibre may lie in the same plane, and the two curved sections of the sheath and portions of the fibre may curve in opposite senses, in a sigmoid configuration (as defined). When they are slid centrally into the channel, they will also lie in the same plane as the longitudinal axis of the channel at that point, but not if (atypically) the plane of the two curved sections of the sheath and portions of the fibre is offset to either side of that axis.

Atypically, such adjustable means may be kept and used in the first, sigmoid configuration (as defined). In that case, light that has initially entered the proximal input end of the first curved section of the sheath and portion of the fibre will exit the fibre through the distal delivery end of the second curved section of the sheath and portion of the fibre in a direction substantially parallel to its initial path on entering the proximal input end of the first curved portion. I If the initial path on entering the proximal input end of the first curved section of the sheath and portion of the fibre lies in a direction parallel to the longitudinal axis of the probe or the channel at or near its distal end, the light exiting the fibre will also be in a direction parallel to the longitudinal axis of the probe or the channel respectively at its distal end.

In the second configuration (larger that the channel of the probe at its narrowest point), the first and second adjacent curved sections of the sheath and portions of the fibre may lie in the same plane, typically beyond the distal end of the channel, and the two curved sections of the sheath and portions of the fibre may curve in the same sense, in a C-configuration.

Again in this case, typically the adjustable means is slid through the channel of the probe from its proximal end to beyond its distal end and expanded into its second configuration.

The light exiting the fibre in from the second curved section may typically lie at the same angle to the longitudinal axis of the probe or the channel respectively at its distal end as it does to its initial path on entering the proximal input end of the first curved portion.

In the second configuration (larger that the channel of the probe at its narrowest point) if the first and second curved sections of the sheath and portions of the fibre are of the same length and curvature through $\theta°$ of circular arc, it will be seen that light that has initially entered the proximal input end of the first curved section of the sheath will exit the adjustable means through the distal delivery end of the second curved section of the sheath in a direction at an angle of $2\times\theta°$ to its initial path on entering the proximal input end of the first curved portion If $\theta°$ is for example 45° of circular arc, it will be seen that light that exits the fibre through the distal delivery end of the second curved section of the sheath will be in a direction orthogonal to its initial path on entering the proximal input end of the first curved section.

In all such forms, when the second curved section of the sheath is rotated about a common axis at a point of adjacency (as defined) from an initial position where it is in a sigmoid configuration with, and in a plane in common with, the first curved section or portion, the direction of light exiting the adjustable means will pass a) from substantially parallel to its initial path on entering the proximal input end of the first curved section of the sheath and portion of the fibre, b) through a series of directions at various angles to, and, depending on the sense of the mutual rotation of the curved sections of the sheath and portions of the fibre on either side of, the initial plane of the section of the sheath and portion of the fibre, c) until, when the second curved section of the sheath has been rotated through 180° from its initial position where it is in a sigmoid configuration to a position where it is in a C configuration with the first curved section of the sheath, the direction of light exiting the adjustable means is skewed to a maximum angle to its initial path on entering the proximal input end of the first curved section of the sheath and portion of the fibre.

In mutual rotation of the curved sections of the sheath about a common central axis, from a sigmoid configuration to a generally C-configuration, the adjacent curved sections of the sheath and portions of the fibre will pass through a series of generally helical configurations under b) above.

Within the scope and spirit of the present invention, a sheath may have n curved sections and portions of fibre of the same length and curvature through $\theta°$ of circular arc. In such general case, it will be seen that light that has initially entered the proximal input end of the first curved section of the sheath will exit the adjustable means through the distal delivery end of the second curved section of the sheath in a direction at a maximum angle of n×θ° to its initial path on entering the proximal input end of the first curved portion.

It may be possible to provide an adjustable means that may be adjusted to other angles of exiting light, depending on the sense of the mutual rotation of the n curved sections of the sheath. If for example there are three identical curved sections of the sheath, each of 30° of circular arc, it will be seen that light that has initially entered the proximal input end of the first curved section of the sheath may exit the adjustable means through the distal delivery end of the third curved section of the sheath in a direction at an angle of 30° or orthogonal to its initial path on entering the proximal input end of the first curved section.

Distinct advantages can be obtained by using this embodiment of this form of the endoscopic probe of the present invention (probe with narrow channel).

As noted above, typically in orthopaedic procedures, the laser beam preferably travels from the delivery end of the adjustable means substantially parallel to the longitudinal axis of the probe at its distal end. In other procedures, it is desirable to direct the exiting beam skewed to the axis of the probe at its distal end, so that, for example soft, tissue which is alongside the probe can be treated.

As will be appreciated, in the above preferred embodiment of this form (probe with narrow channel), the adjustable means may be set, and the probe of the present invention may be used, in any of the series of configurations under a), b) and c) above.

Hence, the angle between light in use of the probe exiting the adjustable means and the longitudinal axis of the probe at its distal end can be readily set at, and varied between, angles required by a wide variety of specific surgical procedures, in particular endoscopic procedures, and a single probe may be used in that wide variety of specific surgical procedures.

Not only that, but the angle between light exiting the adjustable means and the longitudinal axis of the probe at its distal end can be controlled, in particular in endoscopic surgical procedures, to target specific tissue and/or treatment sites.

It is also more economic to fabricate a single probe which may be used in a wide variety of surgical procedures rather than by fabricating a wide variety probes for a wide variety of specific surgical procedures.

The angle between light exiting the adjustable means and the longitudinal axis of the probe at its distal end will depend on the particular surgical procedure contemplated, as different angles will be required by different procedures, as noted above.

Corresponding adjustment of the positions and configurations of the first and second curved sections of the sheath and portions of the fibre relative to each other in the manner described above to achieve these angles between light exiting the adjustable means and the longitudinal axis of the probe at its distal end will be readily deducible by one skilled in the art for a wide variety of probes for endoscopic surgical procedures.

Typical dimensions for a narrow probe and narrow channel for use in, for example laser ablation of the prostate (LAP), such as Holmium Laser Ablation of the Prostate (HoLAP), have been described hereinbefore.

In such endoscopic probes with mutually rotatable first and second adjacent curved sections of a sheath, the typical dimensions for the adjustable means in its first configuration (adjustable means smaller than the channel of the probe at its narrowest point), may be:

5 to 15, for example 5 to 10 mm in overall length (for a straight channel and less for a curved channel, depending on the tightness of the curvature of the channel), and in a transverse direction to the longitudinal axis of the channel at any point, 2 to 6 mm, for example 3 to 5 mm In general, the adjustable means is slid into the channel of the probe from its proximal end to beyond its distal end in its first configuration, and is then is adjusted to the second (larger) configuration.

In its second configuration (larger that the channel of the probe at its narrowest point) in use in a narrow treatment site, for example the prostate, it may be 3 to 9 mm, and for example 5 to 7 mm, in a transverse direction to its longitudinal axis (as defined) at the distal end of the channel and/or the probe.

As noted above, if the channel has any curved parts in which the curvature is relatively tight, the length and the dimension of the adjustable means in use in a transverse direction to a longitudinal axis of the channel at any point may have to be limited to give sufficient transverse play of the adjustable means in the curved section of the elongate channel for the means to be able to negotiate the curved section of the channel.

The design of the probe should be such that the adjustable means does not jam in, and is able to negotiate, any curved section of the channel. The manner in which the design is dictated by the interaction of the dimensions of the bore of the channel and of the curvature of any curved parts of the channel, and the length and the dimension of the adjustable means in its first configuration in a transverse direction to a longitudinal axis at any point of the channel will be known to, or will be readily deducible by, one skilled in the art of endoscopic probe design.

In a fourth, less preferred, embodiment of this form (probe with narrow channel), the adjustable means comprises a rigid, self-supporting curved sheath which is a partial sheath (as defined), in which an open groove in the sheath or a first and/or second curved section supports an optical fibre for delivering light to the delivery end thereof.

The relevant section has at least two securing means, such as arches, spanning the optical fibre to conform the fibre to the sheath or section of the sheath which supports the fibre. The sheath comprises first and second adjacent mutually rotatable curved sections, and either one or both of the first and second adjacent sections of the sheath may have the above partial sheath structure.

The open groove in the sheath or a first and/or second curved section will typically conform to the fibre in the sheath and will have a corresponding cross-section and/or diameter throughout. Its diameter may thus suitably lie in the same ranges as that of a corresponding conduit in a full sheath, depending on the particular optical fibre used.

The number of securing means, such as arches, spanning the optical fibre will depend on the curvature and the length of the relevant curved section, but will usually be three or more.

All other parameters of such a partial sheath and its mutually rotatable first and second adjacent sections of the sheath are as described hereinbefore for the probe of the third, preferred embodiment of this form (probe with narrow channel).

In a fifth, preferred embodiment of this form of the present invention (probe with narrow channel), the adjustable means comprises a rigid, self-supporting curved full sheath, comprising first and second adjacent mutually rotatable curved sections, and one of the first and second adjacent sections of the sheath houses a part of the other section of the sheath. A circumferential sliding bearing is formed where the one section of the sheath houses a part of the other, and the first and second sections of the sheath are mutually rotatable about a common central axis at the sliding bearing. Where the relevant end of the housed section seats fully in the housing section at this bearing, it will also form an axial sliding bearing therebetween.

The sheath closely houses a length of the fibre which is continuous and comprises the first and second adjacent curved portions of the fibre, and holds them curved.

The co-operating internal and external surfaces of the sliding bearing will of course be cylindrical to allow mutual rotation of the curved sections of the sheath about a common central axis, for example in rotation from a sigmoid configuration to a generally C-configuration; or generally helical configurations therebetween.

The outer diameter of the section which is housed in a part of the other section of the sheath may be the same as in the bearing throughout its length. Alternatively, the housed section may have a shoulder abutting the relevant end of the housing curved section first portion at the bearing, and the housing and housed sections may have the same outer diameter throughout their combined lengths. Such a shoulder abutting and co-operating with the opposing surface of the relevant end of the housing curved section may form an annular axial sliding bearing therebetween.

Typical dimensions for an adjustable means, narrow probe and narrow channel of this fifth, preferred embodiment of this form of the invention (probe with narrow channel) are as so described hereinbefore for the probe of the first, preferred embodiment of this form.

Again, the design of the probe should be such that the adjustable means does not jam in, and is able to negotiate, any curved section of the channel. The manner in which the design is dictated by the interaction of the dimensions of the bore of the channel and of the curvature of any curved parts of the channel, and the length and the dimension of the adjustable means in a transverse direction to a longitudinal axis at any point of the channel in its first configuration will be known to, or will be readily deducible by, one skilled in the art of endoscopic probe design.

In this embodiment of this form of the endoscopic probe, the first and second curved sections are of similar, and often the same, low-friction material, at least over a large proportion of the co-operating cylindrical internal and external surfaces of the sliding bearing. It is often convenient, however, for the rest of each integer to be of such materials. A high surface finish on any biocompatible metals may of course be desirable elsewhere than the co-operating internal and external surfaces of the sliding bearing, for reasons of sterility and avoiding the coagulation of bodily fluids on the sheath.

Suitable low-friction materials for use at least over a large proportion of the opposing surfaces of the sliding bearing include those materials so described hereinbefore for integers of the probe of the present invention which are in sliding contact in use with surrounding soft tissue, the adjustable means and/or the channel. Such materials include known low-friction biocompatible plastics materials, such as polytetrafluoroethylene, and known low-friction metallic materials, for example highly surface-finished biocompatible metals, for example biocompatible stainless steels. It may be convenient for the rest of the first and second adjacent curved sections of the sheath to be made of such materials The choice of suitable materials for use in the sheath in the present invention may to some extent depend on the particular surgical procedure contemplated in which this form of the endoscopic probe is to be used, given that the distal end of the sheath will be configured in use to project out of the distal, second end of the elongate channel of the probe (see above), often in contact in use with surrounding tissue.

Either of the internal and external surfaces of the sliding bearing may bear an annular ridge co-operating with an annular groove on the opposing surface of the sliding bearing to limit mutual axial play of the curved sections of the sheath at the bearing. At least one of the surfaces at the annular ridge and/or co-operating annular groove may be of a known resiliently elastic material, for example such a biocompatible plastics material. This arrangement may be used to provide a snap fit between the elements thereof and hence of the curved sections of the sheath at the bearing.

The probe of this second, preferred embodiment of this form (probe with narrow channel) and its first and second adjacent sections of the sheath may be set up and used in endoscopic surgical procedures, for example laser ablation of the prostate, as described hereinbefore for the probe of the third, preferred embodiment of this form.

In a sixth, less preferred, embodiment of the preferred form of the invention (probe with narrow channel), the adjustable means comprises a rigid, self-supporting curved sheath which is a partial sheath (as defined), in which an open groove supports an optical fibre for delivering light to the delivery end thereof.

The sheath comprises first and second adjacent mutually rotatable curved sections, and either one or both of the first and second adjacent sections of the sheath may have the above partial sheath structure. Each section of the sheath also has at least two securing means, such as arches, spanning the optical fibre to conform the fibre to the sheath or section of the sheath which supports the fibre.

As with the fifth, preferred embodiment of this form (probe with narrow channel), one of the first and second adjacent sections of the sheath houses a part of the other section of the sheath to form a circumferential sliding bearing therebetween where the one section of the sheath houses a part of the other, and the first and second sections of the sheath are mutually rotatable about a common central axis at the sliding bearing. Where the relevant end of the housed section seats fully in the housing section at this bearing, it will also form an axial sliding bearing therebetween.

The open groove in the sheath or a first and/or second curved section will typically conform to the fibre in the sheath and will have a corresponding cross-section and/or diameter throughout. Its diameter may thus suitably lie in the same ranges as that of a corresponding conduit in a full sheath, depending on the particular optical fibre used. The number of securing means, such as arches, spanning the optical fibre will depend on the curvature and the length of the relevant curved section, but will usually be three or more.

All other parameters of such a partial sheath and its adjacent mutually rotatable first and second adjacent sections of the sheath are as described hereinbefore for the probe of the first and third, preferred forms of this form.

In a seventh embodiment of the preferred form of the endoscopic probe (probe with narrow channel), the first and second adjacent curved portions of the fibre are separate, but optically connected, integers.

In this embodiment of this form of the endoscopic probe, one of the first and second adjacent sections of the sheath houses a part of the other section of the sheath to form one or more sliding bearing therebetween.

The first and second sections of the sheath are mutually rotatable about a common central axis at the sliding bearing or bearings. It may be convenient for the first and second portions of the fibre to have adjacent planar end surfaces, which are orthogonal to the longitudinal axis of the fibre at the location of the end surfaces.

The first and second adjacent curved portions within the curved sheath may be separated by a plastic transparent index matching material which creates optical coupling, and reduces Fresnel reflection at the interfaces, between the first and second portions. Such a material is preferably formed from, for example, a known liquid, cement (adhesive) or gel, which has an index of refraction that closely approximates to that of the fibre, which is discontinuous within the bearing between the mutually rotatable sections.

The first and second adjacent curved sections of the sheath are mutually rotatable about a common axis at least at the co-operating cylindrical internal and external surfaces of the circumferential sliding bearing between them where one section of the sheath houses a part of the other, as described hereinbefore for the fifth, preferred embodiment of this preferred form (probe with narrow channel).

The configurations of the curved sheath and its first and second adjacent mutually rotatable curved sections are also as described hereinbefore for the second, preferred form; as are their dimensions, for example
the length and curvature of, the corresponding first and second curved sections of the sheath,
the dimension of the sheath in a transverse direction to a longitudinal axis of the channel at any point in use, and
the outer diameters of the section which houses a part of the other section and of the housed part of the other section of the sheath;
and
the materials of which they are made, for example biocompatible plastics materials or biocompatible metallic materials, including those described above with reference to low-friction materials for use at least over a large proportion of the opposing surfaces of any sliding bearing and optionally for the rest of the first and second curved sections of the sheath.

The manner in which the design of the probe is dictated by the interaction of various factors which will be known to, or will be readily deducible by, one skilled in the art of endoscopic probe design. These include, for example the dimensions of the bore of the channel and of the curvature of any curved parts of the channel, and the length and the dimension of the adjustable means in a transverse direction to a longitudinal axis at any point of the channel for the adjustable means in its first configuration not to jam in, and to be able to negotiate, any curved section of the channel In order to ensure good optical coupling between the first and second portions, the housed section preferably has a shoulder abutting the relevant end of the housing curved section portion to form an axial sliding bearing between the housing and housed sections. This axial sliding bearing limits the mutual axial movement of the curved sections of the sheath such that the housed section does not seat fully in the housing section, and leaves a recess space defined by the relevant ends of the housing and housed sections.

The fibre is discontinuous within the bearing between the mutually rotatable sections in this arrangement. The distal end of the first curved portion of the fibre should be flush with the distal end of the first curved section of the sheath within the circumferential sliding bearing between the two sections of the sheath, and the proximal end of the second curved portion of the fibre should be flush with the proximal end of the second curved section of the sheath within the circumferential sliding bearing. The plastic transparent index matching material which creates optical coupling between the first and second portions should be in contact with the two ends of the fibre which is discontinuous across it.

As described above with reference to the fifth, preferred embodiment of the preferred form (probe with narrow channel), in which the fibre is continuous, either of the internal and external surfaces of the circumferential sliding bearing may bear an annular ridge co-operating with an annular groove on the opposing surface. Again, this limits mutual axial play of the curved sections of the sheath at the bearing.

In this arrangement, at least one of the surfaces at the annular ridge and/or co-operating annular groove may be of a known resiliently elastic material, for example such a biocompatible plastics material. This may be used to provide a snap fit between the elements thereof and hence of the curved sections of the sheath at the bearing. As can be appreciated, in this snap-fit version of this embodiment of the endoscopic probe of the present invention, second sections of the sheath of differing lengths and/or configurations thereof, including those described above with reference to other embodiments of the endoscopic probe, may be readily varied and interchanged to give an even more versatile adjustable rigid endoscopic probe.

In this embodiment of the preferred form of the endoscopic probe (probe with narrow channel), the first and second curved sections of the sheath may be of the same length and curvature. However, in general, as can be appreciated, in this snap-fit version of this embodiment of the endoscopic probe of the present invention, second sections of the sheath of differing lengths and/or configurations may be suitable.

This may depend on the particular surgical procedure contemplated, as different maximum angles between light exiting the fibre and the longitudinal axis of the probe at its distal end may depend on the particular surgical procedure contemplated, as different maximum angles to the longitudinal axis of the probe at its distal end may be required by different procedures. Such suitable lengths and/or configurations may include those described above with reference to the other embodiments of this form of the endoscopic probe, of the first and second curved sections.

The probe of this less preferred embodiment of this form (probe with narrow channel) and its first and second adjacent sections of the sheath may be set up and used in endoscopic surgical procedures, for example laser ablation of the prostate, as described hereinbefore for other embodiments of this form.

In a sixth, less preferred, embodiment of this form (probe with narrow channel), the adjustable means comprises a rigid, self-supporting curved sheath which is a partial sheath (as defined).

In this form, an open groove in a first and/or second curved section of the sheath supports an optical fibre for delivering light to the delivery end thereof, and has at least two securing means, such as arches, spanning the optical fibre to conform the fibre to the sheath or section of the sheath which supports the fibre.

The sheath comprises first and second adjacent mutually rotatable curved sections, and either one or both of the first and second adjacent sections of the sheath may have the above partial sheath structure. As with the seventh embodiment of this form, the first and second adjacent curved portions of the fibre are separate, but optically connected integers.

In this embodiment of this form of the endoscopic probe (probe with narrow channel), one of the first and second adjacent sections of the sheath houses a part of the other section of the sheath to form one or more sliding bearing therebetween, and the first and second sections of the sheath are mutually rotatable about a common central axis at the sliding bearing or bearings. It may be convenient for the first and second portions of the fibre to have adjacent planar end surfaces, which are orthogonal to the longitudinal axis of the fibre at the location of the end surfaces.

The first and second adjacent curved portions within the curved sheath may be separated by a plastic transparent index matching material which creates optical coupling, and reduces at the interfaces, between the first and second portions. Such a material is preferably formed from, for example, a known liquid, cement (adhesive) or gel, which has a refractive index that closely approximates to that of the fibre, which is discontinuous within the bearing between the mutually rotatable sections.

The first and second adjacent curved sections of the sheath are mutually rotatable about a common axis at least at the circumferential sliding bearing between them where one section of the sheath houses a part of the other.

The fibre in the sheath will typically conform to the open groove in the first and/or second curved section of the sheath. The groove will have a corresponding cross-section and/or diameter throughout. Its diameter may thus suitably lie in the same ranges as that of a corresponding conduit in a full sheath, depending on the particular optical fibre used. The number of securing means, such as arches, spanning the optical fibre will depend on the curvature and the length of the relevant curved section, but will usually be three or more.

All other parameters of such a partial sheath and its adjacent mutually rotatable first and second adjacent sections of the sheath are as described hereinbefore for the probe of the seventh embodiment of this form (probe with narrow channel).

In a ninth embodiment of the preferred form (probe with narrow channel), the adjustable means comprises a rigid, self-supporting curved full sheath, comprising first and second adjacent mutually rotatable curved sections. Either or both of the first and second sections of the sheath comprises a hollow light guide with a conduit with internally reflective surfaces.

One of the first and second adjacent sections of the sheath houses a part of the other section of the sheath to form a circumferential sliding bearing therebetween where one section of the sheath houses a part of the other, and the first and second sections of the sheath are mutually rotatable about a common central axis at the sliding bearing.

The distal section may house the proximal or vice versa. Where the relevant end of the housed section seats fully in the housing section at this bearing, it will also form an axial sliding bearing therebetween.

As described hereinbefore for the second, preferred embodiment of this form, the housed section preferably has a shoulder abutting the relevant end of the housing curved section portion to embodiment an axial sliding bearing between the housing and housed sections.

In general, in this embodiment of this form both the mutually rotatable sections of the sheath comprise tubular hollow light guides, each with a conduit with internally reflective surfaces. The first and second curved sections of the sheath are preferably of the same length and curvature.

Suitable materials for use in the light guides within the sheath include biocompatible metallic materials, such as stainless steels, with internally reflective surfaces in the conduit with a high surface finish of for example gold coating inside. Preferred light guides in this embodiment of the preferred form include those of biocompatible stainless steels, with inner internally reflective surfaces of gold.

The adjustable means may comprise a sheath in which each section consists essentially of the tubular light guide conduit with internally reflective surfaces. Alternatively, either or both of the first and second sections of the sheath may at least partially house a tubular light guide conduit with internally reflective surfaces. Suitable materials for use in the sheath to surround at least a part of the tubular light guide include known biocompatible plastics materials.

When each section of the sheath consists essentially of a tubular light guide conduit with internally reflective surfaces, one section may be adapted to house a part of the other in a manner which will be known to, or will be readily deducible by, one skilled in the art of endoscopic probe design.

Preferably, however, both of the first and second sections of the sheath each at least partially house a tubular light guide conduit with internally reflective surfaces. The housing and housed parts of the sections, and the circumferential sliding bearing, and the one or two axial sliding bearings therebetween, as described hereinbefore, are then formed in the material which at least partially houses the tubular light guide conduit.

As above, suitable materials for use in the sheath to surround at least a part of the tubular light guide include known biocompatible, self-supporting, low-friction plastics materials which are useful over at least over a large proportion of the opposing surfaces of any sliding bearing, as well as for the rest of the first and second curved sections of the sheath.

As described hereinbefore, the relevant end of the housed section may seat fully in the housing section at the circumferential sliding bearing to form an axial sliding bearing therebetween.

As with the seventh embodiment of this form (probe with narrow channel), the distal end of the first (proximal) light guide should be flush with the distal end of the first curved section of the sheath within the circumferential sliding bearing between the two sections of the sheath, and the proximal end of the second (distal) light guide should be flush with the proximal end of the second curved section of the sheath within the circumferential sliding bearing The tubular light guide conduits within the first and second sections of the sheath then mutually abut at the relevant end of the housed section in register to be optically connected integers which are rotatable about a common central axis.

Alternatively, the housed section of the sheath may be held from seating fully in the housing section at the circumferential sliding bearing, for example by a shoulder abutting the relevant end of the housing curved section portion to form an axial sliding bearing between the housing and housed sections. The resulting recess space defined by the relevant ends of the housing and housed sections then contains a plastic transparent index matching material, which is in contact with the ends of both of, and creates optical coupling, and reduces at the interfaces, between the first and second conduits.

Such a material is preferably formed from, for example, a known liquid, cement (adhesive) or gel, which has an index of refraction that closely approximates to that of the fibre, which is discontinuous within the bearing between the mutually rotatable sections.

Again, as described above with reference to the embodiments of this form (probe with narrow channel) in which the fibre is continuous, either of the internal and external surfaces of the circumferential sliding bearing may bear an annular ridge co-operating with an annular groove on the opposing surface. Again, this limits mutual axial play of the curved sections of the sheath at the bearing.

One of the surfaces at the annular ridge and/or co-operating annular groove may be of a resiliently elastic material, for example such a biocompatible plastics material. This arrangement may be used to provide a snap fit between the elements thereof and hence of the curved sections of the sheath at the bearing.

As can be appreciated, in this snap-fit version of this embodiment of the endoscopic probe of the present invention, second sections of the sheath of differing lengths and/or configurations, including those described above with reference to the first and second forms of the endoscopic probe, may be readily varied and interchanged to give an even more versatile adjustable rigid endoscopic probe.

As above, the adjustable means may comprise a sheath in which each section consists essentially of the tubular light guide conduit with internally reflective surfaces. Alternatively, either or both of the first and second sections of the sheath may at least partially house a tubular internally reflective light guide conduit. In each case, the first, proximal section of the sheath and the fibre are separate, but optically connected integers.

The first, proximal section of the light guide conduit in each case is typically fixedly housed in a short section of sheath, normally at or near its proximal end, and the short section of sheath, normally extends beyond the proximal section of the light guide conduit to fixedly house the fibre at or near its distal end.

As described above with reference to the bearings between the first and second sections of the sheath, the ends of the light guide conduit and the fibre are fixedly housed in register to be optically connected integers, optionally through a plastic transparent index matching material also housed in the short section of sheath, which reduces Fresnel reflection at the interfaces, between the first and second portions.

Such a material is preferably formed from, for example, a gel, which has an index of refraction that closely approximates to that of the fibre, which is discontinuous within the bearing between the mutually rotatable sections. Suitable materials for such use include known materials.

As above, suitable materials for the short section of sheath to surround and fixedly house the ends of the light guide conduit and the fibre include known biocompatible self-supporting, low-friction plastics materials.

In this embodiment of the preferred form of the endoscopic probe (probe with narrow channel), the first and second curved sections of the sheath may be of the same or different lengths and curvatures. All other parameters of such a full sheath and its adjacent mutually rotatable first and second adjacent sections of the sheath are as described hereinbefore for the probe of the seventh embodiment of this form.

In a tenth, less preferred, embodiment of the preferred form (probe with narrow channel), the adjustable means comprises a rigid, self-supporting curved sheath which is a partial sheath (as defined), in which an open groove in either or both of first and/or second mutually rotatable curved sections of the sheath supports a tubular light guide conduit with internally reflective surfaces for delivering light to the delivery end thereof, and has at least two securing means, such as arches, spanning the a tubular light guide conduit to conform the tubular light guide conduit to the sheath or section of the sheath which supports it.

As for the ninth embodiment of the preferred form, one of the first and second adjacent sections of the sheath houses a part of the other section of the sheath to form a circumferential sliding bearing therebetween where one section of the sheath houses a part of the other, and the first and second sections of the sheath are mutually rotatable about a common central axis at the sliding bearing. The distal section may house the proximal and vice versa. Where the relevant end of the housed section seats fully in the housing section at this bearing, it will also form an axial sliding bearing therebetween.

As described hereinbefore for the second, preferred embodiment of this form, the housed section preferably has a shoulder abutting the relevant end of the housing curved section portion to form an axial sliding bearing between the housing and housed sections. The housing and housed parts of the sections, and the circumferential sliding bearing, and the one or two axial sliding bearings therebetween, as described hereinbefore, are formed in the material which at least partially houses the tubular light guide conduit. As above, suitable materials for use in the sheath to support the tubular light guide include known biocompatible plastics materials.

As with the seventh embodiment of this form, the distal end of the first (proximal) light guide should be flush with the distal end of the first curved section of the sheath within the circumferential sliding bearing between the two sections of the sheath. The proximal end of the second (distal) light guide should be flush with the proximal end of the second curved section of the sheath within the circumferential sliding bearing. The relevant end of the housed section may seat fully in the housing section at the circumferential sliding bearing to form an axial sliding bearing therebetween, such that the tubular light guide conduits are optically connected integers which are rotatable about a common central axis.

Alternatively, the housed section of the sheath may be held from seating fully in the housing section at the circumferential sliding bearing, for example by a shoulder abutting the relevant end of the housing curved section portion to form an axial sliding bearing between the housing and housed sections. The resulting recess space defined by the relevant ends of the housing and housed sections then contains a plastic transparent material, which is in contact with the ends of both of, and creates optical coupling between, the first and second tubular light guide conduits.

Again, as described above with reference to the seventh, preferred embodiment of this form, either of the internal and external surfaces of the circumferential sliding bearing may bear an annular ridge co-operating with an annular groove on the opposing surface. Again, this limits mutual axial play of the curved sections of the sheath at the bearing.

One of the surfaces at the annular ridge and/or co-operating annular groove may be of a known resiliently elastic, biocompatible plastics material. This arrangement may be used to provide a snap fit between the elements thereof and hence of the curved sections of the sheath at the bearing.

As can be appreciated, in this snap-fit version of this embodiment of the endoscopic probe of the present invention, second sections of the sheath of differing lengths and/or configurations thereof, including those described above with reference to the first and second forms of the preferred form of the endoscopic probe, may be readily varied and interchanged to give an even more versatile adjustable rigid endoscopic probe.

In this embodiment of the preferred form of the endoscopic probe (probe with narrow channel), the first and second curved sections of the sheath may be of the same or different lengths and curvatures.

The first, proximal section of the light guide conduit is typically fixedly housed in a short section of sheath, normally at or near its proximal end, and the short section of sheath, normally extends beyond the proximal section of the light guide conduit to fixedly house the fibre at or near its distal end. As described above with reference to the bearings between the first and second sections of the sheath, the ends of the light guide conduit and the fibre are fixedly housed in register to be optically connected integers, optionally through a plastic transparent index matching material also housed in the short section of sheath.

As above, suitable materials for the short section of sheath to surround and fixedly house the ends of the light guide conduit and the fibre include known biocompatible plastics materials. These are generally self-supporting, low-friction materials.

In this embodiment of the preferred form of the endoscopic probe, the first and second curved sections of the sheath may be of the same or different lengths and curvatures.

All other parameters of such a full sheath and its adjacent mutually rotatable first and second adjacent sections of the sheath are as described hereinbefore for the probe of the ninth embodiment of this form.

In all embodiments of the present invention in which the adjustable means may be adjusted between first and second configurations in use, by mutually and reversibly rotating two or more parts of the adjustable means, the probe typically comprises means to rotate the second section of the sheath with respect to the first section of the sheath or the first portion of the fibre respectively.

In use, the adjustable means is at the distal delivery end of the fibre and projecting out of the distal, second end of the elongate channel of the probe when it needs to be deployed into its second configuration (larger that the channel of the probe at its narrowest point).

When for example it is in use in a narrow treatment area, it will, depending on the particular surgical procedure be more of less completely surrounded by hard, or more often soft tissue, so that the sections of the sheath will only be accessible from the proximal end of the channel of the probe, and inaccessible from its distal end. The means to rotate the second section of the sheath with respect to the first section of the sheath will thus commonly be operated remotely though the channel of the probe from its proximal end.

As noted above, the sheath may be sheath in which each section consists essentially of a tubular light guide conduit with internally reflective surfaces. Alternatively, either or both of the first and second sections of the sheath may at least partially house a tubular light guide conduit or an optical fibre, in each case with internally reflective surfaces.

The means to rotate the second section of the sheath with respect to the first section of the sheath will thus conveniently comprise a) a second control means attached to or integral with, and extending proximally of the second portion of the sheath beyond the proximal, first end of the channel, and b) a first control means attached to or integral with, and extending proximally of the first portion of the sheath beyond the proximal, first end of the channel, and beyond the proximal end of the second control means.

The means to rotate may for example comprise a a) a second control means in the form of a second tubular sleeve attached to or integral with, and extending proximally of the second portion of the sheath beyond the proximal, first end of the channel, and b) a substantially concentric first control means in the form of a first tubular sleeve attached to or integral with, and extending proximally of the first portion of the sheath beyond the proximal, first end of the channel, and beyond the proximal end of the second control means Each sleeve surrounds at least a part of the fibre proximally of the second portion of the fibre. It has an open proximal, first end and may have an open distal, second end. The second tubular sleeve will pass around the first section of the sheath and the first tubular sleeve up the elongate channel of the probe to beyond its proximal end.

Each sleeve is preferably a cylindrical sleeve with a round cross-section, and in particular a circular, cross-section, especially when each is relatively narrow, since a circular cross-section will tend to reduce the risk of mutually fouling when mutually rotated about their common axis. Each sleeve is preferably of a similar, and especially a uniform, cross-section throughout. Alternatively, both of the first and second sleeves may taper towards their distal ends, but each should then taper at the same rate, especially when each is relatively narrow, since that will also tend to reduce the risk of mutually fouling when mutually rotated about their common axis.

The diameter of a first sleeve of uniform cross-section throughout may suitably lie slightly more than that of the first section of the sheath. The diameter of a second sleeve of uniform cross-section throughout may suitably lie slightly less than that of the first sleeve, but in any even such that the first and second sleeves do no not to jam in mutual rotation of the curved sections of the sheath about a common central, and are able to negotiate, any curved section of the channel.

Each sleeve will typically conform generally to the elongate channel of the probe, and thus where the channel of the probe has a bore which is narrow and/or curved at any point (often near its distal end) it will be appreciated that each sleeve, which is surrounded at least a part by the channel of the probe, should desirably be of a flexible material which can essentially follow any internal curves of the elongate channel of the probe, but is stiff enough for the purpose of sliding the adjustable means into the channel of the probe from its proximal end to at least partially beyond its distal end.

Curvature of any such curved portions will preferably be gradual, since with tight curves in the elongate channel, the means to rotate the second section of the sheath with respect to the first section of the sheath may tend to twist and/or jam between the outer and inner curved faces of the bore of the channel.

The manner in which the design of the probe is dictated by the interaction of various factors which will be known to, or will be readily deducible by, one skilled in the art of endoscopic probe design. These include, for example the dimensions of the bore of the channel and of the curvature of any curved parts of the channel, the length and the dimension of the adjustable means in a transverse direction to a longitudinal axis at any point of the channel, and the length and the dimension of each sleeve in a transverse direction to a longitudinal axis at any point of the channel, and the flexibility of material of which it is made, which should be such that the adjustable means in its first configuration does not to jam in, and is able to negotiate, any curved section of the channel.

To rotate the first and second adjacent sections of the sheath mutually, a) the proximal end of the first tubular sleeve, which is attached to or integral with, and extends proximally of, the first section of the sheath past the proximal end of the second tubular sleeve, is held still, and b) rotating the proximal end of the second tubular sleeve which is attached to or integral with, and extends proximally of, the second section of the sheath past the first section and beyond the proximal, first end of the channel, until the desired configuration of the sheath at the distal end of the channel is achieved.

If space at the proximal end of the elongate channel of the probe allows, mutual rotation of the curved sections of the sheath may be effected by for example using a small constant speed electric motor attached to the proximal end of each sleeve through reduction gearing.

In some forms of the endoscopic probe there is a snap fit between the sections of the sheath and distal sections of the sheath may be interchanged, and the means to mutually rotate the first and second sections about their common axis are substantially concentric first and second tubular sleeves.

In such cases, the outer, second tubular sleeve where it extends proximally of the first section of the sheath and around the first tubular sleeve may conveniently comprise a longitudinal slot running to the proximal end of the outer, second tubular sleeve (whilst the latter still remains attached to or integral with the second section of the sheath). When the second, distal section of the sheath is interchanged, the first section of the sheath and the first tubular sleeve may conveniently be removed from the adjustable means through the longitudinal slot running to the proximal end of the outer, second tubular sleeve and/or from its proximal end.

The above description is directed to adjustable means comprising a sheath which consists essentially of first and second adjacent curved sections which are mutually and reversibly rotatable. It is, however, applicable to any probe with a sheath which comprises more than two curved sections and is suitable for use in a wide or narrow channel mutatis mutandis. The foregoing disclosure is made by way of example only, without in any way limiting the scope and spirit of the present invention.

Thus, each section of such a sheath may have a tubular sleeve attached to or integral with, and extending proximally of the section of the sheath beyond the proximal, first end of the channel, and substantially concentric with the other tubular sleeves. The sleeve attached to or integral with any section of the sheath that is proximal of another section will be housed by, and extend proximally of the proximal end of, the sleeve that is attached to or integral with, the other section of the sheath.

However, it will appreciated that, in general, as the number of sections and sleeves attached to or integral with them increases, it may be difficult to provide an adjustable means that may be readily adjusted between first and second configurations by rotational force applied to the proximal end of the sleeves, especially when each is relatively narrow, since that will tend to increase the risk of mutually fouling or of increasing the total sliding friction between housing and housed sleeves, and/or when the adjustable means comprises an elongate sheath and is used in a relatively narrow elongate and/or curved channel.

Suitable lasers for use with the probe of the present invention will depend on the particular surgical procedure contemplated, as different lasers, laser power levels and/or wavelengths will be required by different procedures. However, in general, suitable laser light sources include in particular Ho:YAG and Nd:YAG lasers, especially such lasers which generate more than 30 watts of laser energy at wavelengths in the two to three micron range, more especially when generated in high energy pulses.

In a second aspect, the present invention provides an optical fibre device for delivering light, which comprises an optical fibre with an input end and a delivery end, with the delivery end characterised by an adjustable means which is adjustable to direct light travelling down the fibre in a desired direction.

The device for delivering light may suitably be used at the distal end of a channel of a conventional endoscopic probe, in particular in an endoscopic surgical probe, especially a narrow probe comprising a narrow elongate channel, such as is often used in laser ablation of the prostate (LAP), such as Holmium Laser Ablation of the Prostate (HoLAP), as described hereinbefore.

In such endoscopic probes, the device may be used in an auxiliary channel (which may be narrow) where it is desired to illuminate the treatment site from various directions using a flexible optical fibre for delivering a visible non-coherent light beam.

However, in general it is used to deliver laser light from a laser device to operate surgically on hard or soft tissue at a treatment site, by using a flexible optical fibre in a working channel (which may be a narrow elongate channel) in the probe The device is suitable to be passed down an elongate channel in a probe until its distal delivery end projects out of the distal end of the elongate channel of the probe. The adjustable means of the device is then adjusted to a configuration which directs light travelling down the fibre which exits the fibre in a desired direction parallel or skewed to the direction in which it initially entered the input end of the means.

In a preferred form, the device is suitable to be passed down a narrow elongate channel from its proximal end to at least partially beyond its distal end, i) a first configuration with a dimension in a transverse direction to the longitudinal axis of the elongate channel of the probe at its narrowest point which is less than the minimum cross-dimension of the channel at that point, where ii) it is changed to a second configuration with a dimension in a transverse direction to the longitudinal axis of the elongate channel of the probe at its distal end which is greater than the above minimum cross-dimension of the channel, which directs light travelling down the fibre in a desired direction.

Suitable and preferred forms, configurations, dimensions, modes of use and forms and embodiments of, and materials for such a device for delivering light include those so described above with reference to the probe and its corresponding components of the first aspect of the present invention.

In a third aspect, the present invention provides a method of treatment which comprises the use of an endoscopic probe of the first aspect of the present invention.

The method of treatment comprises the use of an endoscopic probe of the first aspect of the present invention in operating surgically on hard or soft tissue at a treatment site.

In one form, the method of treatment comprises the use of an endoscopic probe of the first aspect of the present invention to deliver visible non-coherent light to illuminate a treatment site from various directions, by using an adjustable means in an auxiliary channel (which may be narrow) in the probe to illuminate the treatment site from a desired direction.

In another form, the method of treatment comprises the use of an endoscopic probe of the first aspect of the present invention to deliver laser light from a laser device to operate surgically on hard or soft tissue at a treatment site, by using an adjustable means in a working channel (which may be narrow) in the probe to direct the laser light onto the treatment site in a desired direction.

Suitable and preferred forms, configurations, dimensions, modes of use and forms and embodiments of, and materials for such a probe in such a method include those so described above with reference to the probe of the first aspect of the present invention.

More particularly, in the method of surgical treatment of the third aspect of the present invention, the probe delivers laser light from a laser device The method of surgical treatment of the third aspect of the present invention where the elongate channel which in use surrounds at least a large proportion of the optical fibre is narrow comprises i) adjusting the adjustable means to the first configuration (smaller that the channel of the probe at its narrowest point);
ii) sliding the optical fibre, with the adjustable means at its distal delivery end, into the channel of the probe from its proximal end to at least partially beyond its distal end,
iii) adjusting the adjustable means
   a) to the second configuration
   b) so as to direct light travelling down the fibre in any desired direction; and
iv) a) where the light is laser light, treating tissue and/or a treatment site surgically with the laser; or
   b) where the light is non-coherent visible light, illuminating tissue and/or a treatment site with the light, and treating it with surgical equipment.

DESCRIPTION OF THE DRAWINGS

The present invention will now be described with reference to the drawings, but without in any way limiting the scope and spirit of the present invention as defined by the appended claims.

In the Figures:

FIG. 1b is an end view of the distal end of the probe of FIG. 1a.

FIG. 2b is an end view of the distal end of the probe of FIG. 2a.

FIG. 3a. is a longitudinal sectional view of an endoscopic probe in accordance with the present invention with an adjustable means at the distal end of a channel in the probe in a first configuration (transversely smaller that the channel of the probe at its narrowest point), and in which the probe and the channel have a curved portion towards their distal end.

FIG. 3b is an end view of the distal end of the probe of FIG. 3a.

FIG. 4a is a view of the endoscopic probe shown in FIG. 3a with the adjustable means at the distal end of a channel in the probe in a second configuration (transversely larger that the channel of the probe at its narrowest point).

FIG. 4b is an end view of the distal end of the probe of FIG. 4a.

FIGS. 1a and 1b respectively show a longitudinal sectional view and an end view of the distal end of an endoscopic probe (1) in accordance with the present invention for use in laser surgical procedures, having a proximal end (2) and a distal end (3) and comprising a flexible optical fibre (4) having a proximal input end (5) and a distal delivery end (6).

Figure 1A:
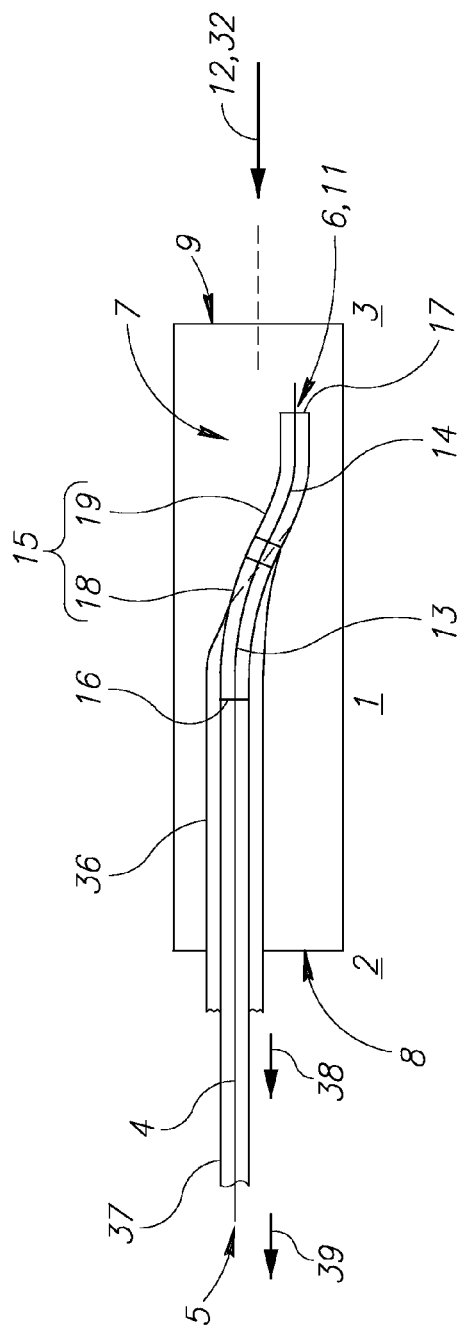
FIG. 1a is a longitudinal sectional view of an endoscopic probe in accordance with the present invention for use in laser surgical procedures, with an adjustable means at the distal end of a channel in the probe in a first configuration (transversely smaller that the channel of the probe at its narrowest point).

The fibre is capable of moving within a channel (7) in the probe (1) between a proximal end (8) and a distal end (9) of the channel (7).

In the probe (1), here shown lying in a position at the distal end (9) of the channel (7), is an adjustable means (10) for directing laser light travelling down the fibre (4) to exit the fibre (4) through a distal end surface (11) thereof in a direction parallel or skewed to a longitudinal axis (12) of the probe (1) at its distal end (3). The adjustable means (10) is mounted on the optical fibre (4) near its distal delivery end (6) and is slidably mounted in the channel (7).

The adjustable means (10) for directing laser light comprises proximal, first (13) and distal, second (14) curved portions of the fibre (4) which are configurable to reflect light travelling down the fibre (4) to exit the fibre through an end surface (11) thereof in a direction parallel or skewed to the longitudinal axis (12) of the probe (1) at its distal end. The means (10) for directing laser light here also comprises a rigid, self-supporting curved sheath (15) with proximal (16) and distal (17) ends, which comprises first, proximal (18) and second, distal (19) adjacent curved sections which are mutually rotatable.

The sheath (15) extends along and closely houses a length of the fibre (4) which comprises the first (13) and second (14) adjacent curved portions of the fibre (4) and holds them curved. At least part (20) of the distal end (17) of the sheath (15) permits the transmission of laser radiation therethrough in use of the probe (1), and is here an aperture, with the distal end (17) of the sheath (15) configured such that it is in register with the distal end (6) of the fibre (4) which it houses.

The probe (1) is shown in FIG. 1a with the sheath (15) and both portions (13, 14) of the fibre (4) surrounded by the channel (7). The first, proximal (18) and second, distal (19) adjacent curved sections of the sheath (15) here have the same dimensions, and configurations (here, they are curved identically) and are formed from the same material, here formed from a biocompatible plastics material or a biocompatible stainless steel.

The adjustable means (10) is in a first configuration, in which it is transversely smaller that the channel (7) of the probe (1). The channel (7) of the probe (1) here has a narrow uniform bore from its proximal end (8) to its distal end (9). (The length of the probe (1) and channel (7) is not to scale.)

In an alternative embodiment of the probe of FIG. 1a, the channel (7) of the probe (1) has a non-uniform bore between its proximal end (8) and its distal end (9), and the adjustable means (10) in the first configuration is transversely smaller that the channel (7) of the probe (1) at its narrowest point.

In this first configuration in the probe of FIG. 1a, the first, proximal (18) and second, distal (19) adjacent curved sections of the sheath (15), and hence the corresponding first and second adjacent curved portions (13, 14) of the fibre (4), are curved identically in opposite senses. They are lying in the same plane in a sigmoid configuration (as defined hereinbefore). The adjustable means (10) then has a dimension in the transverse direction which is at a minimum.

Figure 1B:
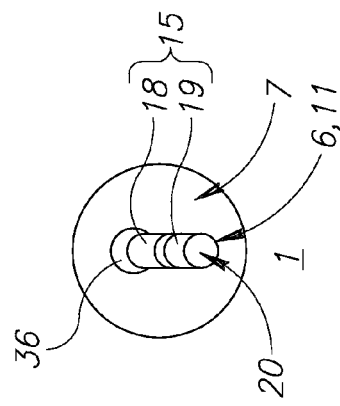

If the adjustable means (10) lies centrally in the channel (7) of the probe (1) at its distal end (8) as shown in FIG. 1b, the first (18) and second, distal (19) adjacent curved sections of the sheath (15) in this form also lie in the same plane as the longitudinal axis (32) of the channel (7) at its distal end (9) (here coincident with the longitudinal axis (12) of the probe (1) at its distal end (3)).

Figure 5:
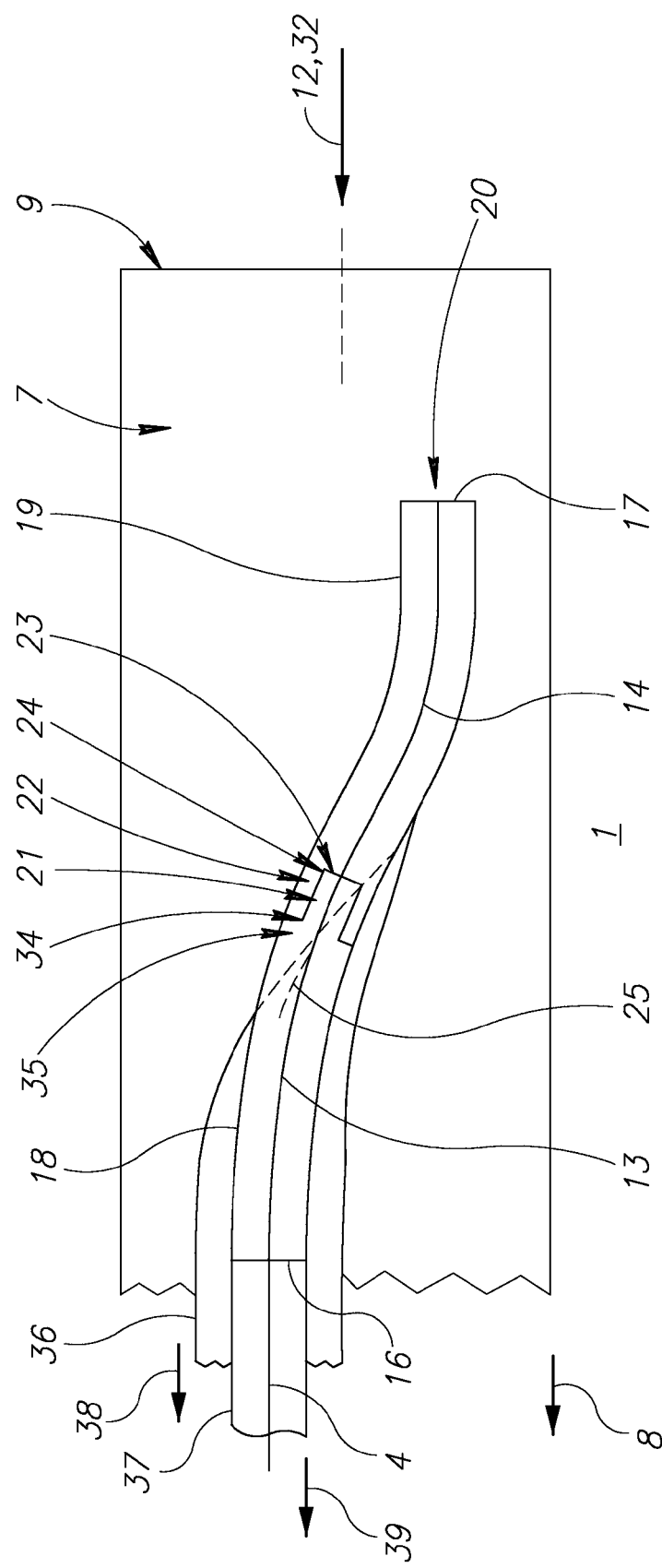
FIG. 5 is a longitudinal sectional view of part of the continuous optical fibre of the probe of FIG. 1a, at a bearing between mutually rotatable sections of a sheath in the adjustable means at the distal end of the channel of the probe.

As shown in FIG. 1a, and in greater detail in FIG. 5, in the adjustable means (10), there is at least one bearing between mutually rotatable sections (18, 19) of the sheath (15) around the continuous optical fibre (4) of the probe (1). The proximal part (22) of the distal section (19) of the sheath (15) slidably houses a distal part (21) of the proximal section (18) of the sheath (15).

There is an axial sliding bearing (23) where the first (18) and second (19) sections of the sheath (15) abut at the distal part (21) of the first (18) section of the sheath (15). There is also an annular axial sliding bearing (34) formed by a shoulder (35) at the distal part (21) of the first section (18) of the sheath (15) abutting and co-operating with an opposing surface of the proximal part (22) of the distal section (19).

There is further a circumferential sliding bearing (24) where the first (18) section of the sheath (15) is housed in the second section (19). The two sections (18,19) are mutually rotatable about a common central axis (25) at the sliding bearings (23,24,34).

In an alternative embodiment of the probe of FIG. 1a (not shown), the distal part (21) of the proximal section (18) of the sheath (15). slidably houses the proximal part (22) of the distal section (19) of the sheath (15). The two sections (18,19) are again mutually rotatable about a common central axis (25) at the same sliding bearings (23,24,34) between corresponding surfaces of the first and second curved sections (18,19) of the sheath mutatis mutandis.

There is thus a circumferential sliding bearing (24) where the first (18) section of the sheath (15) houses the second section (19), and an axial sliding bearing (23) where the first (18) and second (19) sections of the sheath (15) abut at the distal part (21) of the first (18) section of the sheath (15). There is also an annular axial sliding bearing (34) formed by a shoulder (35') at the proximal part (22) of the distal section (19) abutting and co-operating with an opposing surface of the distal part (21) of the first section (18) of the sheath (15).

Although not shown in FIG. 1a or in FIG. 5, in the adjustable means (10), in the circumferential sliding bearing (21) between the mutually rotatable sections (18, 19) of the sheath (15), ether surface of the bearing (24) may bear an annular ridge co-operating with an annular groove on the opposing surface of the bearing (24). This limits mutual axial play of the first section (18) and second section (19) of the sheath (15).

At least one of the surfaces at the annular ridge and/or co-operating annular groove may be of a known resiliently elastic biocompatible plastics material. This arrangement may be used to provide a snap fit between the curved first section (18) and second section (19) of the sheath (15).

The first (18) and second (19) adjacent curved sections of the sheath (15) have means to rotate the second section (19) of the sheath (15) with respect to the first section (18), here
a) a second manual control means in the form of a second tubular sleeve (36) attached to or integral with, and extending proximally of the second section (19) of the sheath beyond the proximal, first end (8) of the channel (7), and
b) a first manual control means in the form of a substantially concentric first tubular sleeve (37) attached to or integral with, and extending proximally of the first section (18) of the sheath (15) beyond the proximal, first end (8) of the channel (7), and beyond the proximal end (38) of the second control means (36)

In use, the adjustable means (10) is put in its first configuration, with the first (18) and second (19) adjacent curved sections of the sheath (15) lying in the same plane in a sigmoid configuration (as defined). The adjustable means (10) is then slid into the channel (7) of the probe (1) from its proximal end (8) to at least partially beyond its distal end (9).

This is effected by means of the first sleeve (37). This sleeve is of a known material which is flexible where it surrounds at least a part of the first section (18) of the sheath (15), but where it surrounds the part of the fibre (4) proximally of the first section (18) of the sheath (15) is stiff enough for the purpose of sliding the adjustable means (10) into the channel (7) of the probe (1) from its proximal end (8) to at least partially beyond its distal end (9).

Figure 2A:
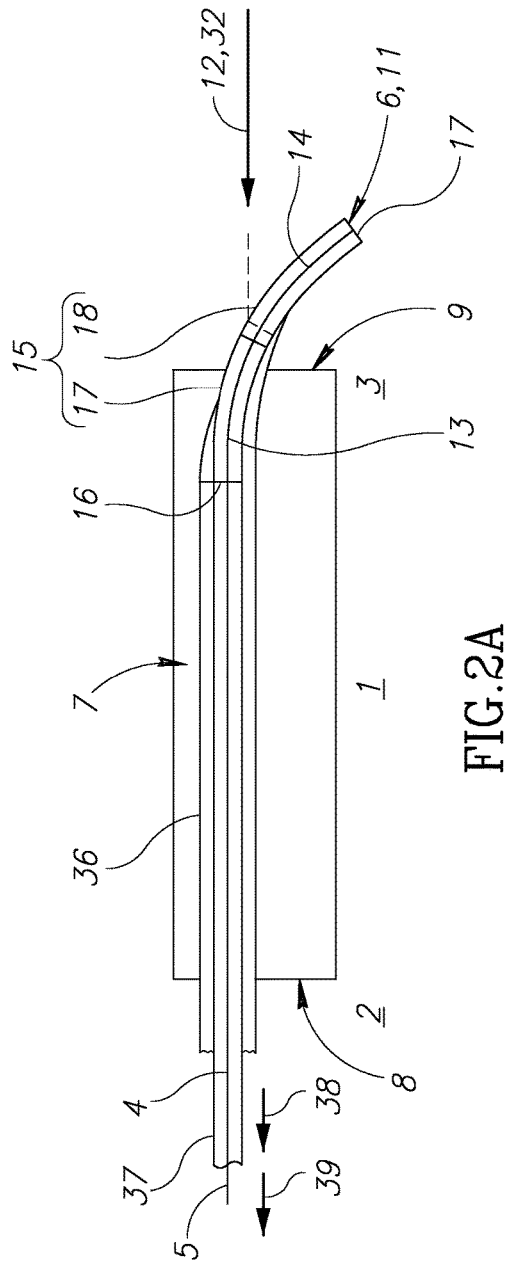
FIG. 2a is a view of the endoscopic probe shown in FIG. 1a with the adjustable means at the distal end of a channel in the probe in a second configuration (transversely larger that the channel of the probe at its narrowest point, and projecting out of the channel.
Figure 2B:
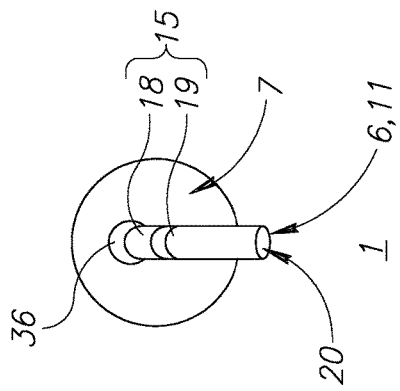

As shown in FIGS. 2a and 2b, when it is at least partially beyond the distal end (9) of the channel (7) of the probe (1), the adjustable means (10) is deployed from its first configuration, with the first (18) and second (19) adjacent curved sections of the sheath (15) lying in the same plane in a sigmoid configuration (as in FIG. 1a) to its ultimate second configuration, a generally C-configuration.

This is achieved by mutual rotation of the sections (18, 19) of the sheath (15) around the common central axis (25) at the sliding bearings (23,24,34) between corresponding surfaces of the first and second curved sections (18,19) of the sheath (15), in turn effected by
a) holding still the proximal end (39) of the first tubular sleeve (37), which is attached to or integral with, and extends proximally of, the first section (18) of the sheath (18) past the proximal end (38) of the second tubular sleeve (36), and
b) rotating the proximal end (38) of the second tubular sleeve (36) which is attached to or integral with, and extends proximally of, the second section (19) of the sheath past the first section (18) and beyond the proximal, first end (8) of the channel (7), until the desired configuration of the sheath (15) at the distal end (9) of the channel (8) is achieved.

Although not shown in FIG. 1a or in FIG. 2a, it will be appreciated that mutual rotation of the sections (18, 19) of the sheath (15) around the common central axis (25) at the sliding bearings (23,24,34) therebetween, effected as described above, alters the adjustable means (10) from its first configuration to its ultimate second configuration, during which it causes the distal end (17) of the sheath (15), projecting out of the distal end (9) of the channel (8), to describe a circular path in a plane orthogonal to the common central axis (25) at the sliding bearings (24,25, 26).

It also causes the sheath (15) to adopt a series of generally helical configurations between the first configuration and the ultimate second configuration of the adjustable means (10).

In FIG. 2a, light that has initially entered the proximal input end (5a) of the first curved portion (13) of the fibre (4) will exit the fibre (4) through the distal delivery end (20) of the second curved portion (14) in a direction skewed to its initial path on entering the proximal input end (5a) of the first curved portion (13), and to the longitudinal axis (12) of the probe (1) and the longitudinal axis (32) of the channel (7) at their distal ends (3,9). Light exiting the fibre is at an angle to the longitudinal axis of the probe at its distal end of about 45°.

In alternative embodiments of the probe of FIG. 2a the angle to the longitudinal axis of the probe at its distal end of may suitably be between 30 and 90°, for example 40 and 70°.

Although also not shown in FIG. 1a or FIG. 2a, the probe (1) may be used in any of the intermediate configurations between the first configuration and second configuration, of the adjustable means (10) generated during mutual rotation of the sections (18, 19) of the sheath (15) around the common central axis (25) at the sliding bearings (23,24,34) therebetween. This can direct light travelling down the fibre (4) which exits the fibre through its distal end surface (11) thereof in further desired directions skewed to the longitudinal axis (12) of the probe (1) at its distal end (3).

The above steps are reversed to alter the adjustable means (10) from its second configuration to its first configuration, and to remove the adjustable means (10) from the channel (7) of the probe (1), for example after any laser surgical procedure, from the second configuration through the first configuration.

FIGS. 3a, b and 4a, b show an endoscopic probe (1) in accordance with the present invention with an adjustable means (10) at the distal end (9) of a channel (8). The probe (1) and its operation are generally similar to that of FIG. 1a, but the probe (1) and the channel (8) each have a curved part (33) towards their distal ends (3, 9).

FIG. 3a shows the endoscopic probe (1) with the distal end (17) of the sheath (15) around a waveguide in the form of a continuous optical fibre (4) in the adjustable means (10) in a first configuration (transversely smaller than the channel (7) of the probe (1) just projecting out of the distal end (9) of the channel (8). The channel (7) of the probe (1) has a bore which is narrow, and the channel (7) and the probe (1) near the distal end (9) of the channel (7) have a curved part (33). The curvature of the curved part (33) is gradual. (The length of the probe (1) and channel (7) is not to scale.)

As shown in FIG. 3a, the fibre (4) in the adjustable means (10) projecting out of the distal end (9) of the channel (8) runs in a direction substantially parallel to its initial path on entering the proximal end (16) of the first curved section (18) of the sheath (15). The initial path of the fibre (4) entering the proximal end (16) of the first curved section (18) of the sheath (15) and of the fibre (4) its distal end (6) are each in a direction parallel to the longitudinal axis (12) of the probe (1) at its distal end (3).

In an alternative embodiment of the probe of FIG. 3a, the channel (7) of the probe (1) is narrower and/or curves more tightly than that shown. It will be seen that the path of the fibre (4) entering the proximal end (16) of the first curved section (18) of the sheath (15) and of the fibre (4) its distal end (6) will each be in a direction skewed towards the longitudinal axis (12) of the probe (1) at its distal end (3). This will be so until the point of adjacency (31) between the two sections (18, 19) of the sheath (15) is beyond the distal end (3) of the probe (1) while the adjustable means (10) is still in its first configuration (as above).

The elongate channel (8) should not be too narrow or curve too tightly with respect to the length and dimension in a transverse direction to a longitudinal axis of the channel (7) at all points in the channel (7). If it is, the sheath (15) may not readily follow any internal curves of the elongate channel (7), and it may tend to twist and/or jam between the outer and inner curved faces of the bore of the channel (8).

Similarly, the sleeve (36), although of a material which is flexible where it surrounds at least a part of the first section (18) of the sheath (19), may also not readily follow any internal curves of the elongate channel (7), and it may tend to twist and/or jam between the outer and inner curved faces of the bore of the channel (8).

As described above for FIGS. 1 and 2, in use, the adjustable means (10) is put in its first configuration, with the first (18) and second (19) adjacent curved sections of the sheath (15) lying in the same plane in a sigmoid configuration (as defined). The adjustable means (10) is then slid into the channel (7) of the probe (1) from its proximal end (8) to at least partially beyond its distal end (9). Again, this is effected by means of the first sleeve (37). This sleeve is here of a known material which is flexible but stiff enough for the purpose of inserting the adjustable means (10).

It is then deployed into its ultimate second configuration (transversely larger that the channel (8) of the probe (1), and projecting out of the distal end (9) of the channel (8), in a generally C-configuration, as shown in FIG. 4. This is achieved by mutual rotation of the sections (18, 19) of the sheath (15) around the common central axis (25) at the sliding bearings (23,24,34) between cooperating surfaces of the first and second curved sections (18,19) of the sheath (15).

This, in turn, is effected by mutual rotation of the first tubular sleeve (37), which is attached to or integral with, and extends proximally of, the first section (18) of the sheath (15), and the second tubular sleeve (36) which is attached to or integral with, and extends proximally of, the second section (19) of the sheath (15), as described above.

Again, alteration of the adjustable means (10) from its first configuration to its ultimate second configuration gives rise to intermediate configurations between the first configuration and second configuration, of the adjustable means (10) during mutual rotation of the sections (18, 19), in which the probe (1) may be used to direct light travelling down the fibre (4) which exits the fibre through its distal end surface (11) thereof in further desired directions skewed to the longitudinal axis (12) of the probe (1) at its distal end (3).

The above steps are reversed to alter the adjustable means (10) from its second configuration to its first configuration, and to remove the adjustable means (10) from the channel (7) of the probe (1) distal end (17) of the sheath (15), projecting out of the distal end (.

Figure 6:
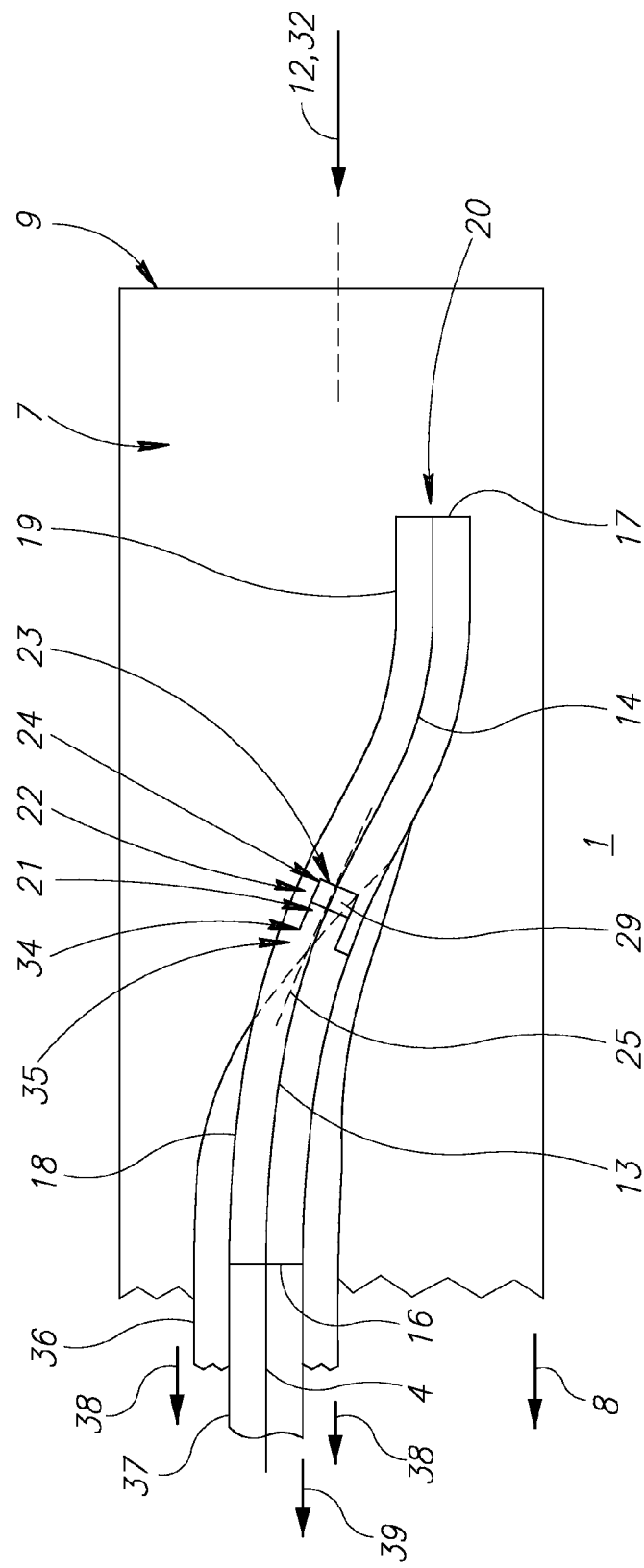
FIG. 6 is a longitudinal sectional view of part of the optical fibre of a probe similar to that of FIG. 1a, but with a fibre which is discontinuous at a bearing between mutually rotatable sections of a sheath in the adjustable means at the distal end of the channel of the probe.

FIG. 6 shows an adjustable means (10) on a part of an optical fibre (4) lying in a position at the distal end (9) of a channel (7) of a probe (1) similar to that shown in FIG. 1*a*, and in greater detail in FIG. 5, except that within the adjustable means (10) near the axial bearing (36) between the mutually rotatable sections (18, 19) of the sheath (15) the fibre (4) is discontinuous.

Similarly to the adjustable means (10) shown in FIG. 5, at the distal part (21) of the first (18) section of the sheath (15), there is an annular axial sliding bearing (34) formed by a shoulder (35) at the distal part (21) of the proximal section (18) abutting and co-operating with an opposing surface of the proximal part (22) of the distal section (19) of the sheath (15). This axial sliding bearing limits the mutual axial movement of the curved sections (18, 19) of the sheath (15) such that the proximal section (18) does not seat fully in the distal section (19), and leaves a recess space (28) defined by the respective ends of the sections (18,19).

The fibre (4) is discontinuous within the bearing (24) between the mutually rotatable sections (18,19). The distal end of the first curved portion (13) of the fibre is flush with the distal end of the first curved section (18) of the sheath (15) within the circumferential sliding bearing (24) between the two sections (18,19) of the sheath (15), and the proximal end of the second curved portion of the fibre (14) should be flush with the proximal end of the second curved section (19) of the sheath within the circumferential sliding bearing (24).

A known plastic transparent index matching material (29), which creates optical coupling between the first and second portions (13,14) fills the recess space (28) defined by the respective ends of the sections (18,19) and is in contact with the two ends of the fibre (4) which is discontinuous across it.

In an alternative embodiment of the probe of FIG. 6 (not shown), the distal part (21) of the proximal section (18) of the sheath (15). slidably houses the proximal part (22) of the distal section (19) of the sheath (15). The two sections (18,19) are again mutually rotatable about a common central axis (25) at the same sliding bearings (23,24,34) between corresponding surfaces of the first and second curved sections (18,19) of the sheath mutatis mutandis.

There is thus a circumferential sliding bearing (24) where the first (18) section of the sheath (15) houses the second section (19), and an axial sliding bearing (23) where the first (18) and second (19) sections of the sheath (15) abut at the distal part (21) of the first (18) section of the sheath (15).

There is also an annular axial sliding bearing (34) formed by a shoulder (35') at the proximal part (22) of the distal section (19) abutting and co-operating with an opposing surface of the distal part (21) of the first section (18) of the sheath (15).

As in FIG. 5, within the adjustable means (10), there is also a circumferential sliding bearing (24) between the mutually rotatable sections (18, 19) of the sheath (15). Either surface of the bearing (24) may bear an annular ridge co-operating with an annular groove on the opposing surface of the bearing (24) to limit mutual axial play of the first section (18) and second section (19) of the sheath (15). At least one of the surfaces at the annular ridge and/or co-operating annular groove may be of a known resiliently elastic material, biocompatible plastics material. This arrangement may be used to provide a snap fit between the curved first section (18) and second section (19) of the sheath (15).

The second section (19) of the sheath (15) has means to rotate it with respect to the first section (18), here a manual control means attached to, and extending from, the second section (19) of the sheath (15) beyond the proximal, first end (8) of the channel (7).

The means to rotate is here a tubular sleeve (36) of a flexible material, which surrounds at least a part of the first section (18) of the sheath (15) and a part of the fibre (4) proximally of the first section (18) of the sheath (15).

As shown, in the adjustable means (10) on a part of an optical fibre (4) lying in a position at the distal end (9) of a channel (7) of a probe (1), within the adjustable means (10) near the axial bearing (23) between the mutually rotatable sections (18, 19) of the sheath (15) the fibre (4) is discontinuous.

In another alternative embodiment of the probe of FIG. 1*a*, the two sections (18, 19) of the sheath (15) may not necessarily have the same curvature or dimensions. For example the respective dimension along their curves; the second, distal section (19) may for example curve less or more tightly than the first, proximal section (18).

It will preferably curve more than the first section (18), in particular when used in a channel (7) of the probe (1) which is relatively narrow, since that will tend to reduce the dimension of the adjustable means (10) in a transverse direction to a longitudinal axis of the channel (12) at any point, when in its first configuration (transversely smaller that the channel (12) of the probe (1).

It will be appreciated that in this embodiment of the endoscopic probe (1), the fibre (4) at the bearing (23) is discontinuous, the sliding fit between the mutually rotatable sections (18, 19) of the sheath (15); and the optional snap fit between the curved sections of the sheath (15) mean that different distal sections (19) may be interchanged. Such distal sections (19) may differ from each other in their respective curvature and/or dimensions, for example the respective dimension along their curves.

This will further extend the number of different desired directions of light exiting the fibre (4) skewed to the longitudinal axis (12) of the probe (1) at its distal end (3) that may be achieved. In turn, this may extend by the number of configurations, ways and different procedures, for example laser surgical procedures, in which the endoscopic probe (1) in accordance with the present invention may be used with such an adjustable means (10) at the distal end (9) of its channel (8).

Where, as here, the means to rotate the second, distal section (19) is a tubular sleeve (36) of a flexible material which surrounds at least a part of the first section (18) and is attached to or integral with the second, distal section (19), the tubular sleeve may conveniently comprise a longitudinal slot (30).

To interchange two second, distal sections (19), the adjustable means (10) is withdrawn from the proximal end (8) of the channel (7) in the probe (1), and in a first configuration (transversely smaller than the channel (7) of the probe (1)). If the means to rotate the second, distal section (19) is a tubular sleeve attached to the second, distal section (19), it is conveniently detached. The second, distal section (19) is then slid off the first, proximal section (18), a different second, distal section (19) is then slid onto the first, proximal section (18), and the means to rotate the second, distal section (36) is reattached to the second, distal section (19).

The adjustable means (10) is slid generally longitudinally into the proximal end (8) of the channel (7) in the probe (1), in a first configuration (transversely smaller than the channel (7) of the probe (1)). If the means to rotate the second, distal section (19) is a tubular sleeve integral with the second, distal section (19), the tubular sleeve may conveniently comprise a longitudinal slot (30), as noted above.

The procedure with, and configurations of, the adjustable means (10) when slid longitudinally out of or into the proximal end (8) of the channel (7) in the probe (1) as described above with reference to the form of the endoscopic probe (1) in which the means to rotate, a tubular sleeve (36), is attached to the second, distal section. In the present instance, it may be convenient to use the longitudinal slot (30), noted above, in the interchange of two second, distal sections (36) for better access and to allow some transverse play of the fibre (4) during the procedure.

Figure 7:
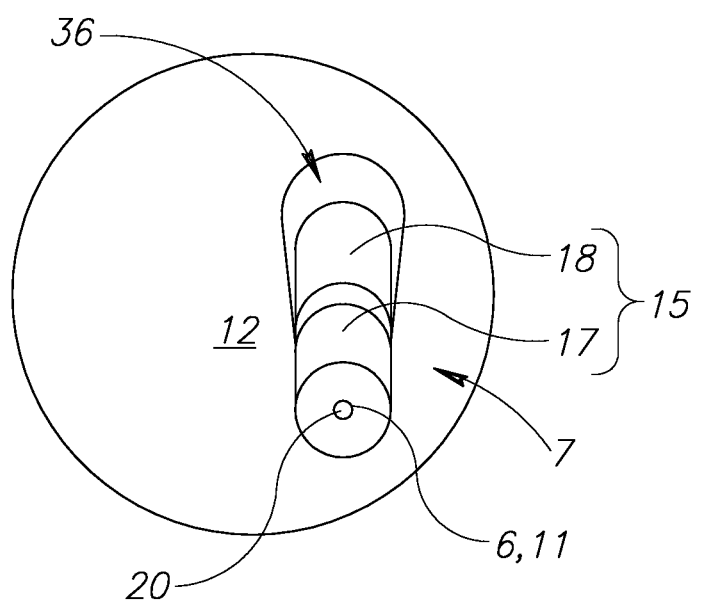
FIG. 7 is an end view of the distal end of a probe similar to that of FIG. 1a, but with a larger-diameter channel in the probe and the adjustable means offset to one side of the longitudinal axis of the channel at its distal end.

FIG. 7 is an end view of the distal end of a probe similar to that of FIG. 1a, but the adjustable means (10), here in a first configuration, with the first (18) and second (19) adjacent curved sections of the sheath (15) are lying in the same plane in a sigmoid configuration (as defined), but set to one side of, and not in the same plane as the longitudinal axis (12) of the probe (1) at its distal end (3)).

Light that has initially entered the proximal input end (5a) of the first curved portion (13) of the fibre (4) will exit the fibre (4) through the distal delivery end (2) of the second curved portion (14) in a direction substantially parallel to its initial path on entering the proximal end (16) of the first curved section (18) of the sheath (15).

If the initial path on entering the proximal input end (5a) of the first curved portion (13) also lies in a direction parallel to the longitudinal axis (12) of the probe (1) at its distal end (3), the light exiting the fibre will also be in a direction parallel to the longitudinal axis (12) of the probe (1) at its distal end, as noted above.

The invention claimed is:

1. An endoscopic probe, having a proximal end and a distal end and having one or more channels therethrough;
   an optical fiber having a proximal input end and a distal delivery end, the optical fiber being capable of moving within one of the one or more channels in the probe,
   the delivery end of the fiber further comprising an adjustment mechanism for directing and redirecting light travelling down the fiber such that the light exits the fiber through the delivery end of the adjustment mechanism in a desired direction,
   the adjustment mechanism comprising a rigid, self-supporting curved sheath at least partially surrounding and encompassing the fiber and having proximal and distal ends, the distal end including first, proximal and second, distal adjacent curved sections which are mutually rotatable with respect to one another around the optical fiber;
   further comprising a first tubular sleeve, the first tubular sleeve having a proximal end portion and a distal end portion,
   a second tubular sleeve, the second tubular sleeve at least partially surrounding the first tubular sleeve in the vicinity of its distal end portion to the vicinity of its proximal end portion;
   the second tubular sleeve being rotatable with respect to the first tubular sleeve;
   wherein the distal portion of the first tubular sleeve is connected to the proximal portion of the first section of the sheath,
   wherein the distal portion of the second tubular sleeve is connected to the proximal portion of the second section of the sheath, and
   whereupon, upon actuation of the adjustment mechanism by rotation of the second tubular sleeve with respect to the first tubular sleeve, the second section of the curved sheath rotates relative to the first section of the curved sheath and the shape of the distal end changes from one shape to another shape.

2. An endoscopic probe as recited in claim 1 wherein the curved sections have the same length and curvature.

3. An endoscopic probe as recited in claim 1 wherein the fiber is integral through its first and second portions.

4. An endoscopic probe as recited in claim 1 wherein at least part of the distal end of the sheath permits the transmission of radiation therethrough in use of the probe.

5. An endoscopic probe as recited in claim 4 wherein the distal end of the sheath is configured such that it is in register with the distal end of the fiber which it houses.

6. An endoscopic probe as recited in claim 4 wherein the distal end of the sheath is an aperture.

7. An endoscopic probe as recited in claim 1 wherein one of the first and second adjacent curved sections of the sheath houses a part of the other section of the sheath to form a circumferential sliding bearing therebetween, and the first and second sections of the sheath are mutually rotatable about a common central axis at the sliding bearing.

8. An endoscopic probe as recited in claim 7 wherein the second, distal section of the sheath houses a part of the first, proximal section of the sheath to provide a circumferential sliding bearing therebetween, and the first and second sections of the sheath are mutually rotatable about a common central axis at the sliding bearing.

9. An endoscopic probe as recited in claim 7 wherein the first, proximal section of the sheath houses a part of the second, distal section of the sheath to provide a circumferential sliding bearing therebetween, and the first and second sections of the sheath are mutually rotatable about a common central axis at the sliding bearing.

10. An endoscopic probe as recited in claim 7 wherein the first, proximal and second, distal section of the sheath has adjacent planar end surfaces, which are orthogonal to the longitudinal axis of the sheath at the location of the end surfaces, abut in an axial sliding bearing therebetween, and are mutually rotatable about a common central axis at the sliding bearing.

11. An endoscopic probe as recited in claim 7 wherein either surface of the bearing bears an annular ridge co-operating with an annular groove in the opposing surface of the bearing.

12. An endoscopic probe as recited in claim 11 wherein the surface at the annular ridge and/or co-operating annular groove is of a resiliently elastic material.

13. An endoscopic probe as recited in claim 1 wherein the first and second portions of the fiber are discontinuous.

14. An endoscopic probe as recited in claim 13 wherein the first and second portions of the fiber have adjacent planar end surfaces, which are orthogonal to the long axis of the fiber at the location of the end surfaces, abut in a transverse sliding bearing therebetween, and are mutually rotatable about a common central axis at the sliding bearing.

15. An endoscopic probe as recited in claim 13 wherein the first and second adjacent curved portions of the fiber are separated by a plastic transparent index matching material which creates optical coupling between the first and second portions.

16. An endoscopic probe as recited in claim 15, wherein the ends of the first and second portions of the fiber are flush with the respective ends of the curved section of the sheath at the circumferential sliding bearing, the section of the sheath which is housed in the other section of the sheath has a shoulder abutting the relevant end of the housing curved section to form an axial sliding bearing between the housing and housed sections, such that the housed section does not seat fully in the housing section, and leaves a recess space defined by the ends of the housing and housed sections, and the transparent index matching material which creates optical coupling between the first and second portions of the fiber fills the recess space.

17. An endoscopic probe as recited in claim 1 wherein the second tubular sleeve comprises a manual control to rotate the second tubular sleeve with respect to the first tubular sleeve.

18. An endoscopic probe as recited in claim 1, wherein the shape of the distal end of the device changes from a sigmoid shape to a C-shape, or from a C-shape to a sigmoid shape.

19. An endoscopic probe as recited in claim 1 wherein the sheath is formed from a biocompatible plastics material or a biocompatible stainless steel.

20. An endoscopic probe as recited in claim 1 wherein the endoscopic probe is a surgical endoscopic probe, the fiber is used to deliver laser radiation to its distal end, and the channel is a working channel of the probe.

21. A method of treatment which comprises the use of an endoscopic probe as recited in claim 1.

22. A method of treatment as recited in claim 21 which comprises the use of the probe to deliver one or more of visible non-coherent light or laser light from a laser device to illuminate a treatment site from various directions using the visible non-coherent light, or to operate surgically on hard or soft tissue at a treatment site with the laser light, by using an adjustable means in an auxiliary channel in the probe to illuminate the treatment site from a desired direction using non-coherent light or to direct the laser light onto the treatment site in a desired direction.

23. A method of surgical treatment as recited in claim 22 where the channel in use surrounds at least a large proportion of the optical fibre and is narrow which comprises
  i) adjusting the adjustable means to a first configuration (smaller than the channel of the probe at its narrowest point);
  ii) sliding the optical fibre, with the adjustable means at its distal delivery end, into the channel of the probe from its proximal end to at least partially beyond its distal end,
  iii) adjusting the adjustable means
    a) to a second configuration (larger that the channel of the probe at its narrowest point)
    b) so as to direct light travelling down the fiber which exits the fibre through its delivery end in any desired direction; and
  iv) a) where the light is laser light, treating tissue and/or a treatment site surgically with the laser; or
    b) where the light is non-coherent visible light, illuminating tissue and/or a treatment site with the light, and treating it with surgical equipment.

* * * * *